(12) United States Patent
Miekka et al.

(10) Patent No.: US 7,252,799 B2
(45) Date of Patent: Aug. 7, 2007

(54) METHODS FOR STERILIZING PREPARATIONS CONTAINING ALBUMIN

(75) Inventors: Shirley I. Miekka, Gaithersburg, MD (US); Wilson Burgess, Clifton, VA (US); William N. Drohan, Springfield, VA (US); Martin J. Macphee, Montgomery Village, MD (US); Randall S. Kent, Thousand Oaks, CA (US); David M. Mann, Gaithersburg, MD (US); Yuri Griko, Gaithersburg, MD (US)

(73) Assignee: Clearant, Inc., Los Angeles, CA (US)

( * ) Notice: Subject to any disclaimer, the term of this patent is extended or adjusted under 35 U.S.C. 154(b) by 204 days.

(21) Appl. No.: 09/942,941

(22) Filed: Aug. 31, 2001

(65) Prior Publication Data

US 2003/0213920 A1  Nov. 20, 2003

(51) Int. Cl.
*A61K 38/46* (2006.01)
*A61K 39/395* (2006.01)

(52) U.S. Cl. ............... 422/22; 424/94.6; 424/94.1; 424/176.1; 422/21; 422/23

(58) Field of Classification Search ............ 422/30, 422/176, 21, 23, 22; 435/375, 188, 2
See application file for complete search history.

(56) References Cited

U.S. PATENT DOCUMENTS

| | | |
|---|---|---|
| RE23,195 E | 2/1950 | Brasch |
| 2,832,689 A | 4/1958 | Proctor et al. |
| 2,920,969 A | 1/1960 | Stoddard |
| 2,962,380 A | 11/1960 | Wertheim |
| 3,620,944 A | 11/1971 | Tanito |
| 3,743,480 A | 7/1973 | Falk |
| 3,779,706 A | 12/1973 | Nablo |
| 3,962,038 A | 6/1976 | Kawashima et al. .......... 195/68 |
| 4,136,094 A | 1/1979 | Condie |
| 4,251,437 A | 2/1981 | Rasmussen et al. |
| 4,282,863 A | 8/1981 | Beigler et al. |
| 4,330,626 A | 5/1982 | Blair et al. |
| 4,336,247 A | 6/1982 | Eriksen |
| 4,370,264 A | 1/1983 | Kotitschke et al. |
| 4,409,105 A | 10/1983 | Hayashi et al. |
| 4,472,840 A | 9/1984 | Jefferies |
| 4,620,908 A | 11/1986 | Van Duzer |

(Continued)

FOREIGN PATENT DOCUMENTS

CA  2056619  10/1991

(Continued)

OTHER PUBLICATIONS

AABB FDA Liaison Meeting, ABC Newsletter, Dec. 12, 1997, pp. 14.

(Continued)

*Primary Examiner*—David Vanore
*Assistant Examiner*—Johnnie L Smith, II
(74) *Attorney, Agent, or Firm*—Morgan, Lewis & Bockius LLP

(57) ABSTRACT

Methods are disclosed for sterilizing preparations containing albumin to reduce the level of one or more active biological contaminants or pathogens therein, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. These methods involve sterilizing preparations containing albumin, such as plasma protein fractions, with irradiation.

38 Claims, 23 Drawing Sheets

Gamma Irradiation of Dried and Powder PPF

U.S. PATENT DOCUMENTS

| | | | |
|---|---|---|---|
| 4,727,027 A | 2/1988 | Wiesehahn et al. | 435/173 |
| 4,784,850 A | 11/1988 | Abraham | |
| 4,798,611 A | 1/1989 | Freeman, Jr. | |
| 4,865,602 A | 9/1989 | Smestad et al. | |
| 4,877,866 A | 10/1989 | Rudnick et al. | 530/387 |
| 4,894,253 A | 1/1990 | Heineman et al. | 427/36 |
| 4,931,361 A | 6/1990 | Baldeschwieler et al. | |
| 4,933,145 A | 6/1990 | Uchida et al. | |
| 4,946,648 A | 8/1990 | Dichtelmüller et al. | |
| 4,963,356 A | 10/1990 | Calenoff et al. | |
| 4,994,237 A | 2/1991 | Login et al. | 422/21 |
| 5,000,951 A | 3/1991 | Bass et al. | |
| 5,002,766 A | 3/1991 | Ransberger et al. | 424/94.2 |
| 5,012,503 A | 4/1991 | Nambu et al. | |
| 5,044,091 A | 9/1991 | Ueda et al. | |
| 5,106,619 A | 4/1992 | Wiesehahn et al. | |
| 5,134,295 A | 7/1992 | Wälischmiller | |
| 5,185,371 A | 2/1993 | Rubinstein | |
| 5,226,065 A | 7/1993 | Held et al. | |
| 5,283,034 A | 2/1994 | Okrongly et al. | |
| 5,362,442 A | 11/1994 | Kent | |
| 5,418,130 A | 5/1995 | Plat. et al. | |
| 5,460,962 A | 10/1995 | Kemp | |
| 5,510,122 A | 4/1996 | Sreebny et al. | |
| 5,548,066 A | 8/1996 | Leneau et al. | |
| 5,603,894 A | 2/1997 | Aikus et al. | |
| 5,609,864 A | 3/1997 | Shanbrom | |
| 5,637,451 A * | 6/1997 | Ben-Hur et al. | 435/2 |
| 5,643,464 A | 7/1997 | Rhee et al. | |
| 5,712,086 A | 1/1998 | Horowitz et al. | |
| 5,730,933 A * | 3/1998 | Peterson | 422/22 |
| 5,798,238 A * | 8/1998 | Goodrich et al. | 435/173.3 |
| 5,817,528 A | 10/1998 | Böhm et al. | |
| 5,837,313 A | 11/1998 | Ding et al. | |
| 5,856,172 A | 1/1999 | Greenwood et al. | |
| 5,881,534 A | 3/1999 | Ahlqvist et al. | |
| 5,911,951 A | 6/1999 | Girardot et al. | 422/28 |
| 5,955,256 A * | 9/1999 | Sowemimo-Coker et al. | 435/2 |
| 5,958,669 A | 9/1999 | Ogle et al. | 435/1.1 |
| 5,965,349 A | 10/1999 | Lin et al. | 435/2 |
| 5,981,163 A * | 11/1999 | Horowitz et al. | 435/4 |
| 5,986,168 A | 11/1999 | Noishiki | |
| 5,989,498 A * | 11/1999 | Odland | 422/22 |
| 6,010,719 A | 1/2000 | Remon et al. | |
| 6,046,024 A | 4/2000 | Burton et al. | |
| 6,049,025 A | 4/2000 | Stone et al. | |
| 6,060,233 A | 5/2000 | Wiggins | |
| 6,066,626 A | 5/2000 | Yew et al. | |
| 6,087,141 A | 7/2000 | Margolis-Nunno et al. | |
| 6,120,592 A | 9/2000 | Brault et al. | |
| 6,159,490 A | 12/2000 | Deghenghi | |
| 6,171,549 B1 * | 1/2001 | Kent | 422/22 |
| 6,187,572 B1 | 2/2001 | Platz et al. | |
| 6,190,855 B1 | 2/2001 | Herman et al. | |
| 6,197,207 B1 | 3/2001 | Chapman et al. | |
| 6,203,544 B1 | 3/2001 | Gotzen | |
| 6,214,534 B1 | 4/2001 | Horowitz et al. | |
| 6,235,508 B1 * | 5/2001 | Sowemimo-Coker et al. | 435/173.1 |
| 6,258,821 B1 | 7/2001 | Stogniew et al. | |
| 6,277,337 B1 * | 8/2001 | Goodrich et al. | 422/186.3 |
| 6,312,931 B1 | 11/2001 | O'Dwyer et al. | 435/173.1 |
| 6,346,216 B1 * | 2/2002 | Kent | 422/22 |
| 6,358,284 B1 | 3/2002 | Fearnot et al. | 623/23.72 |
| 6,375,989 B1 | 4/2002 | Badylak et al. | 424/551 |
| 6,383,732 B1 | 5/2002 | Stone | 435/1.1 |
| 6,383,810 B2 | 5/2002 | Fike et al. | 435/384 |
| 6,384,419 B1 | 5/2002 | Purtle | 250/526 |
| 6,461,630 B1 | 10/2002 | Tucker et al. | 424/423 |
| 6,485,723 B1 | 11/2002 | Badylak et al. | 424/93.7 |
| 6,635,222 B2 * | 10/2003 | Kent | 422/22 |
| 6,682,695 B2 * | 1/2004 | MacPhee et al. | 422/22 |
| 6,696,060 B2 * | 2/2004 | Grieb et al. | 424/176.1 |
| 6,749,851 B2 * | 6/2004 | Mann et al. | 424/94.6 |
| 6,783,968 B2 * | 8/2004 | Drohan et al. | 435/200 |
| 6,908,591 B2 * | 6/2005 | MacPhee et al. | 422/22 |
| 6,946,098 B2 * | 9/2005 | Miekka et al. | 422/22 |
| 2001/0049141 A1 | 12/2001 | Fike et al. | 435/384 |
| 2002/0015662 A1 * | 2/2002 | Hlavinka | 422/24 |
| 2002/0064807 A1 | 5/2002 | Badylak et al. | 435/34 |
| 2002/0106394 A1 | 8/2002 | Tucker et al. | 424/423 |
| 2002/0188319 A1 | 12/2002 | Morris et al. | 606/213 |
| 2003/0068815 A1 | 4/2003 | Stone et al. | 435/325 |
| 2003/0095890 A1 * | 5/2003 | Miekka et al. | 422/22 |
| 2003/0194806 A1 * | 10/2003 | Lin et al. | 435/404 |

FOREIGN PATENT DOCUMENTS

| | | |
|---|---|---|
| EP | 310 316 | 4/1989 |
| EP | 334 679 | 9/1989 |
| EP | 919 918 A2 | 6/1999 |
| EP | 919 918 A3 | 6/1999 |
| EP | 0808167 B1 | 6/2002 |
| EP | 0820301 B1 | 7/2002 |
| JP | 408098688 A | 4/1996 |
| JP | 11-216147 | 8/1999 |
| SU | 1321420 A | 7/1987 |
| WO | WO 90/00907 | 2/1990 |
| WO | WO 91/16060 | 10/1991 |
| WO | WO 95/03071 | 2/1995 |
| WO | WO 00/25839 | 3/2000 |
| WO | WO 00/28552 | 5/2000 |
| WO | WO 00/52031 | 9/2000 |
| WO | WO 01/08611 A1 | 2/2001 |
| WO | WO 01/12318 A1 | 2/2001 |
| WO | WO 01/3211 A2 | 5/2001 |
| WO | WO 01/32107 A2 | 5/2001 |
| WO | WO 01/45720 A1 | 6/2001 |
| WO | WO 01/49219 A1 | 7/2001 |
| WO | WO 01/72233 A1 | 10/2001 |
| WO | WO 01/72244 A1 | 10/2001 |
| WO | WO 01/91818 A1 | 12/2001 |

OTHER PUBLICATIONS

Ozan Akkus et al., Fracture Resistance of Gamma Radiation Sterilized Cortical Bone Allografts, 2001, pp. 927-934, Journal of Orthopaedic Research, vol. 19.

Tikvah Alper et al., The Exceptionally Small Size of the Scrapie Agent, 1966, pp. 278-284, Biochemical and Biophysical Research Communications, vol. 22, No. 3.

Tikvah Alper et al., Protection by Anoxia of the Scrapie Agent and Some DNA and RNA Viruses Irradiated as Dry Preparations, 1968, pp. 157-166, J. Gen. Virol., vol. 3.

Tikvah Alper et al., Does the Agent of Scrapie Replicate Without Nucleic Acid? May 20, 1967, pp. 764-766, Nature, vol. 214.

Tikvah Alper et al., The Scrapie Agent: Evidence Against its Dependence For Replication on Intrinsic Nucleic Acid, 1978, pp. 503-516, J. Gen. Virol., vol. 41.

S.R. Aparicio et al., Light and Electron Microscopy Studies on Homograft and Heterograft Heart Valves, 1975, pp. 174-162, J. Path, vol. 115.

J. Baksa et al., The Use of Pig's Skin (xenograft) for the Treatment of Burns, 1976, pp. 138-145, Magyar Traumatologin, vol. 19.

Michael L. Baldwin et al., Irradiation of Blood Components, 1992, pp. 10-78, American Association of Blood Banks.

R.H. Bassin et al., Abrogation of Fv-1$^b$Restriction With Murine Leukemia Viruses Inactivated by Heat or by Gamma Irradiation, May 1978, pp. 306-315, Journal of Virology, vol. 26, No. 2.

Guy Beauregard et al., Temperature Dependence of the Radiation Inactivation of Proteins, 1985, pp. 117-120, Analytical Biochemistry, vol. 150.

Sandra Blakeslee, Tight Rules on Use of Organs Do Not Apply to Tissues, Jan. 20, 2002, The New York Times Newspaper.

Seymour S. Block, Disinfection, Sterilization, and Preservation, Fundamental Principles of Activity Principles of Antimicrobial Activity, Fourth Edition, 1991, pp. 31-33.

A.J.J.C. Bogers et al., Long-Term Results of the Gamma-Irradiation-Preserved Homograft Monocusp for Transannular Reconstruction of the Right-Ventricular Outflow Tract in Tetralogy of Fallot, 1994, pp. 337-330, Thorac. Cardiovasc. Surgeon, vol. 42.

David R. Brown et al., Antioxidant Activity Related to Copper Binding of Native Prion Protein, 2001 pp. 69-76, Journal of Neurochemistry, vol. 76.

P. Brown, The Risk of Blood-Borne Creutzfeldt-Jakob Disease, 1999, pp. 53-59, Advances in Transfusion Safety Dev. Biol. vol. 102.

P. Brown et al., Further Studies of Blood Infectivity in an Experimental Model of Transmissible Spongiform Encephalopathy, With an Explanation of Why Blood Components Do Not Transmit Creutzfeldt-Jakob Disease in Humans, Nov./Dec. 1999, pp. 1169-1178, Transfusion, vol. 39.

Paul Brown et al., Effect of Chemicals, Heat, and Histopathologic Processing on High-Infectivity Hamster-Adapted Scrapie Virus, May 1982, pp. 683-687, The Journal of Infectious Diseases, vol. 145, No. 5.

P. Brown et al., The Distribution of Infectivity in Blood Components and Plasma Derivatives in Experimental Models of Transmissible Spongiform Encephalopathy, Sep. 1998, pp. 810-816, Transfusion, vol. 38.

D.G. Campbell et al., Sterilization of HIV With Irradiation: Relevance to Infected Bone Allografts, 1999, pp. 517-521, Aust. N.Z.J. Surg., vol. 69.

Ernest U. Conrad et al., Transmission of the Hepatitis-C Virus by Tissue Transplantation, Feb. 1995, pp. 214-224, The Journal of Bone and Joint Surgery, vol. 77-A, No. 2.

A.S. Dagli, Correction of Saddle Nose Deformities by Coral Implantation, 1997, pp. 274-276, Eur. Arch. Otorhinolaryngol, vol. 254.

Defeng et al., Sterilization of Silver-Acidum Pipemedicum Skin for the Treatment of Burns by Radioactive Cobalt-60-,Gamma.-Ray, 1995, pp. 406 (Abstract).

P. Di Simplicio et al., The Reactivity of the SH Group of Bovine Serum Albumin With Free Radicals, 1991, pp. 253-262, Free Rad. Res. Comms., vol. 14, No. 4.

R.J. Donnelly et al., Gamma-radiation of Heart Valves at 4 ° C; A Comparative Study Using Techniques of Histochemistry and Electron and Light Microscopy, 1973, pp. 95-101, Thorax, vol. 28.

Duane C. Eichler et al., Radiation Inactivation Analysis of Enzymes, Jul. 15, 1987, pp. 9433-9436, The Journal of Biological Chemistry, vol. 262, No. 20.

Luanne H. Elliott et al., Inactivation of Lassa, Marburg and Ebola Viruses by Gamma Irradiation, Oct. 1982, pp. 704-708, Journal of Clinical Microbiology, vol. 16, No. 4.

Bradley M. Fideler et al., Gamma Irradiation: Effects on Biomechanical Properties of Human Bone-Patellar Tendon-Bone Allografts, 1995, pp. 643-646, American Journal of Sports Medicine, vol. 23, No. 5.

Bradley M. Fideler et al., Effects of Gamma Irradiation on the Human Immunodeficiency Virus, Jul. 1994, The Journal of Bone and Joint Surgery, vol. 76-A, No. 7.

Fields et al., Susceptibility of Scrapie Agent to Ionizing Radiation, Apr. 5, 1969, pp. 90-91, Nature, vol. 222.

M.J. Gibbons et al., Effects of Gamma Irradiation on the Initial Mechanical and Material Properties of Goat Bone-Patellar Tendon-Bone Allografts, 1991, pp. 209-218, J. Orthop Res, vol. 9, No. 2.

J.R.P. Gibbons et al., Gamma Ray Sterilisation of Homograft Valves, 1969, pp. 353-358, Bulletin De La Societe Internationale De Chirugie, No. 3.

M.J. Goertzen et al., Anterior Cruciate Ligament Reconstruction Using Cryopreserved Irradiated Bone-ACL-Bone-Allograft Transplants, 1994, pp. 150-157, Knee Surgery Sports Traumatology Arthroscopy, vol. 2.

M.J. Goertzen et al., Sterilisation of Canine Anterior Cruciate Allografts by Gamma Irradiation in Argon, Mar. 1995, pp. 205-212, The Journal of Bone and Joint Surgery, vol. 77-B, No. 2.

Slawomir Gregorczyn et al., Strength of Lyophilized and Irradiated Cortical Bone of the Human Femur, 1995, pp. 129-133, Chir. Narz. Ruchu Ortop. Pol., Lx 2.

D.A. Haig, Further Studies on the Inactivation of the Scrapie Agent by Ultraviolet Light, 1969, pp. 455-457, J. Gen. Virol., vol. 5.

F.W. Hehrlein et al., Biochemische Veränderungen an Heterologen Aortenklappentransplantaten nach Anwendung Verschiedener Sterilisationsverfahren, pp. 1183-1185, Langenbecks Arch. Chir., Bd. 325 (Kongrebericht) (English Summary found at p. 1183).

F.W. Hehrlein et al., Morphologische Utersuchungen an Heterologen Herzklappentransplantaten Unter Verschiedenen Sterilisationsbedingungen, pp. 244-251 (English Summary found at p. 250).

H. Hiemstra et al., Inactivation of Human Immunodeficiency Virus by Gamma Radiation and its Effect on Plasma and Coagulatin Factors, 1991, pp. 32-39, Transfusion, vol. 31, No. 1.

Richard Hinton et al., A Biomechanical Analysis of Solvent-dehydrated and Freeze-Dried Human Fascia Lata Allografts, 1992, pp. 607-612, The American Journal of Sports Medicine, vol. 20, No. 5.

B. Horowitz et al., Inactivation of Viruses in Labile Blood Derivatives, II. Physical Methods, 1985, pp. 523-527, Transfusion, vol. 25, No. 6.

M. Horowitz, Sterilization of Homograft Ossicles by Gamma Radiation, Nov. 1979, pp. 1087-1089, The Journal of Laryngology and Otology, vol. 93.

Carol House et al., Inactivation of Viral Agents in Bovine Serum by Gamma Irradiation, 1990 pp. 737-740, Can. J. Microbiol., vol. 36.

Shinichiro Ijiri et al., Effect of Sterilization on Bone Morphogenetic Protein, 1994, pp. 628-636, Journal of Orthopaedic Research, vol. 12.

A.S. Imamaliev et al., Biological Properties of Bone Tisue Conserved in Plastic Material and Sterilized With Gama Rays, 1974, pp. 129-135, ACTA, Chirurgiae Plasticae, vol. 16, No. 3.

A. Ingegneri et al., An 11-Year Assessment of 93 Flash-frozen Homograft Valves in the Aortic Position, 1979, pp. 304-307, Thorac. Cardiovasc. Surgeon, vol. 27.

J. Jerosch et al., A New Technique for Bone Sterilization, 1989, pp. 117-120, Biomedizinische Technik, Band 34, Heft 5.

J. Jerosch et al., Influence of Different Rehydration Periods on the Stability and the Water Content of Bone Allografts After Lyophilization, Gamma-Irradiation, and Lipid Extraction, 1994, pp. 335-341, Z. Orthop., vol. 132.

J.D. Keathley et al., Is There Life After Irradiation? Part 2: Gamma-Irradiated FBS in Cell Culture Jul./Aug. 1993, pp. 46-52, BioPharm.

E.S. Kempner et al., Size Determination of Enzymes by Radiation Inactivation, 1979, pp. 2-10, Analytical Biochemistry, vol. 92.

L. Kerboull et al., In Vitro Study of the Influence of Avrious Conservation Methods on the Mechanical Properties of Patellar Tendon Allografts, 1991, pp. 751-762, Chirurgie, vol. 117.

A.D. Kitchen, Effect of Gamma Irradiation on the Human Immunodeficiency Virus and Human Coagulation Proteins, 1989, pp. 223-229, Vox Sang, vol. 56.

Andrezej Komender et al., Some Biological Properties of Bovine Trypsinized Fascia Xenografts, 1981, pp. 485-489, Archivum Immunologiae et Therapiae Experimentalis, vol. 29.

Andrezej Komendar et al., Some Biological Properties of Preserved Bovine Fascia Enrighed With Pulverized Calf Cartilage, 1984, pp. 211-219, Archivum Immunologiae et Therapiae Experimentalis, vol. 32.

J.F. Kouvalchouk et al., The Use of Sterilized Bone Allografts in Reconstruction After Tumour Resection, 1986, pp. 393-401, Revue de Chirurgie Orthopedique, vol. 72.

Raymond Latarjet, Inactivation of the Agents of Scrapie, Creutzfeldt-Jakob Disease, and Kuru by Radiations, 1979, pp. 387-407, Slow Transmissible Diseases of the Nervous System, vol. 2.

R. Latarjet et al., Inactivation of the Scrapie Agent by Near Monochromatic Ultraviolet Light, Sep. 26, 1970, pp. 1341-1343, Nature, vol. 227.

Douglas C. Lee et al., A Direct Relationship Between the Partitioning of the Pathogenic Prion Protein and Transmissible Spongiform Encephalopathy Infectivity During the Purification of Plasma Proteins, Apr. 2001, pp. 449-455, Transfusion, vol. 41.

Susan F. Leitman, Use of Blood Cell Irradiation in the Prevention of Posttransfusion Graft-vs-Host Disease, 1989, pp. 219-232, Transfus. Sci., vol. 10.

Linberg et al., Irradiated Homologous Cartilage For Orbital Reconstruction, Jul. 1980, pp. 457-462, Ophthalmic Surgery, vol. 11.

Sandra McDowell, Irradiated Cartilage, Spring 1988, pp. 14-15, Plastic Surgical Nursing.

A. Maeda et al., Effects of Solvent Preservation With or Without Gamma Irradiation on the Material Properties of Canine Tendon Allografts, 1993, pp. 181-189, Journal of Orthopaedic Research, vol. 11.

Akira Maeda et al., Solvent-dried and Gamma-irradiated Tendon Allografts in Rats, Jul. 1998, pp. 731-736, The Journal of Bone and Joint Surgery, vol. 80-B, No. 4.

S. Malawski et al., The Use of Dry-Freezed Bone Grafs Sterilized by Gamma Rays in Orthopaedic Surgery, 1969, pp. 61-68, Chir. Narz. Ruchu Ortop.

Linda Marton et al., Disinfection and Inactivation of the Human T. Lymphotrogic Virus Type III/Lymphadenopathy-Associated Virus, Aug. 1985, pp. 499-403, The Journal of Infectious Diseases, vol. 151, No. 2.

S.I. Miekka et al., New Methods for Inactivation of Lipid-enveloped and Non-enveloped Viruses, 1998, pp. 402-408, Haemophilia, vol. 4.

Ken Nakata et al., Reconstruction of the Lateral Ligaments of the Ankle Using Solvent-dried and Gamma-Irradiated Allogeneic Fascia Lata, May 2000, pp. 579-582.

Maria Esther Martinez Pardo et al., Clinical Application of Amniotic Membranes on a Patient With Epidermolysis Bullosa, 1999, pp. 68-73, Annals of Transplantation, vol. 4, No. 3-4.

Jan Parizek et al., Duraplasty With Pretreated Freeze-Dried Sterilized Human Dura Mater, 1990, pp. 135-143, Sbor. ved. Praci LF UK Hradee Kralove, vol. 33.

Jan Parizek et al., Ovine Pericardium: A New Material For Duraplasty, 1996, pp. 508-513, J. Neurosurg., vol. 84.

Patel et al., Effect of Gamma Radiation and Ethylene Oxide on Papain, 1979, pp. 81-83, Indian. J. Pharm. Sci., vol. 41, No. 2.

L.V. Polezhaeu et al., Repair of Cranial Defects With Regenerating Bone in Grafting Gamma-Irradiated Bone Filings, pp. 57-60.

Pollard, The Effect of Ionizing Radiation on Viruses, pp. 65-71.

Donald J. Prolo et al., Composite Autogeneic Human Cranioplasty: Frozen Skull Supplemental With Fresh Iliac Corticocancellous Bone, Dec. 1984, pp. 846-851, Neurosurgery, vol. 15, No. 6.

Donald J. Prolo et al., Superior Osteogenesis in Transplanted Allogeneic Canine Skull Following Chemical Sterilization, Aug. 1982, pp. 230-242, Clinical Orthopaedics and Related Research, No. 168.

Elena Quaglio et al., Copper Converts the Cellular Prion Protein Into a Protease-resistant Species That Is Distinct From the Scrapie Isoform, Apr. 6, 2001, pp. 11432-11438, The Journal of Biological Chemistry, vol. 276, No. 14.

T.J. Rasmussen et al., The Effects of 4 Mrad of Gamma-Irradiation on the Initial Mechanical Properties of Bone-Patellar Tendon-Bone Grafts, 1994, pp. 188-197, The Journal of Arthroscoic and Related Surgery, vol. 10, No. 2.

Brian D. Reid, The Sterways Process: A New Approach to Inactivating Viruses Using Gamma Radiation, 1998, pp. 125-130, Biologicals, vol. 26.

S.C. Roe et al., The Effect of Gamma Irradiation on a Xenograft Tendon Bioprothesis, 1992, pp. 149-154, Clinical Materials, vol. 9.

Robert G. Rohwer, Estimation of Scrapie Nucleic Acid MW From Standard Curves for Virus Sensitivity to Ionizing Radiation, Mar. 27, 1986, pp. 381, Nature, vol. 320, No. 6060.

Robert G. Rohwer, Scrapie Infectious Agent is Virus-like in Size and Susceptibility to Inactivation, Apr. 12, 1984, pp. 658-662, Nature, vol. 308.

R.G. Rohwer, The Scrapie Agent: A Virus by Any Other Name, pp. 195-232, Current Topics in Microbiology and Immunology, vol. 172.

Robert G. Rohwer et al., Scrapie-Virus or Viroid, The Case For A Virus, pp. 333-355, Laboratory of Central Nervous System Studies, National Institutes of Neurological and Communicative Disorders and Stroke, National Institutes of Health.

Robert G. Rohwer, Virus-Like Sensitivity of the Scrapie Agent to Heat Inactivation, Feb. 10, 1984, pp. 600-602, Science, vol. 223.

Robert Sullivan et al., Inactivation of Thirty Viruses by Gamma Radiation, Jul. 1971, pp. 61-65, Applied Microbiology, vol. 22, No. 1.

D. Tylman, Mechanical Character of Liofilized and Sterilized by Gamma-Rays Bone Tissue, 1996, pp. 229-234, Chirurgia Narzadow Ruchu I, Ortopedia Polska.

W. Welch, A Comparative Study of Different Methods of Processing Aortic Homografts, 1969, pp. 746-749, Thorax, vol. 24.

J.M. White et al., Sterilization of Teeth by Gamma Radiation, Sep. 1994, pp. 1560-1567, J. Dent. Res., vol. 73, No. 9.

Boon-Seng Wong et al., Copper Refolding of Prior Protein, 2000, pp. 1217-1224, Biochemical and Biophysical Research Communications, vol. 276.

Boon-Seng Wong et al., Differential Contribution of Superoxide Dismutase Activity by Prior Protein in Vivo, 2000, pp. 136-139, Biochemcial and Biophysical Research Communications, vol. 273.

Boon-Seng Wong et al., Prion Disease: A Loss of Antioxidant Function? 2000, pp. 249-252, Biochemical and Biophysical Research Communications, vol. 275.

D.E. Wyatt et al., Is There Life After Irradiation? Part I: Inactivation of Biological Contaminants, Jun. 1993, pp. 34-39, BioPharm.

Qi Zhang et al., Ethylene Oxide Does Not Extinguish the Osteoinductive Capacity of Demineralized Bone, 1997, pp. 104-108, Acta Orthop Scand, vol. 68, No. 2.

Yongxing Zhang et al., A Comprehensive Study of Physical Parameters, Biomechanical Properties and Statistical Correlations of Iliac Crest Bone Wedges Used in Spinal Fusion Surgery, 1994, pp. 304-308, Spine, vol. 19, No. 3.

License Amendment and procedures for Gamma Irradiation of Blood Products, Jun. 22, 1993, pp. 1-18, Dept. of Health & Human Services, Food and Drug Administration.

M.F. Alladine et al., γ-Radiation Damage to Starr-Edwards Valves, Mar. 16, 1998, pp. 68, The Lancet, Letters to the Editor.

Ch. Baquey et al., Radiosterilization of Albuminated Polyester Prostheses, May 1987, pp. 185-189, Biomaterials, vol. 8.

Edward H. Bedrossian, Jr., HIV and Banked Fascia Lata, 1991, pp. 284-288, Ophthalmic Plastic and Reconstructive Surgery, vol. 7, No. 4.

Liu Bingci, Mouse Antibody Response Following Repetitive Injections of Gamma-Irradiated Human Placenta Collagen, Jun. 1994, pp. 100-103, Chinese Medical Sciences Journal, vol. 9, No. 2.

A.A. Belov et al., The Influence of γ-Radiation on Enzyme Activity of Collalitin in the Process of Storage, Dec. 7, 1989, pp. 519-521, All-Union Research Institute of Textile and Haberdashery Industry, Moscow.

R.G. Burwell, The Fate of Freeze-Dried Bone Allografts, Jun. 1976, pp. 95-111, Transplantation Proceedings, vol. VII, No. 2, Supplement 1.

L. Callegaro et al., Hollow Fiber Immobilized L-Asparaginase: In Vivo and In Vitro Immunological Studies, 1983, pp. 91-96, The International Journal of Artificial Organs, vol. 6, No. 2.

G. Campalani et al., Aortic Valve Replacement With Frozen Irradiated Homografts, 1989, pp. 558-561, Eur. J. Cardio-thoracic Surgery, vol. 3.

David T. Cheung et al., The Effect of γ-Irradiation on Collagen Molecules, Isolated α-chains, and Crosslinked Native Fibers, 1990, pp. 581-589, Journal of Biomedical Materials Research, vol. 24.

David J. Cohen et al., The Fate of Aortic Valve Homografts 12 to 17 Years After Implantation, Mar. 1988, pp. 482-484, Chest, vol. 93, No. 3.

A.G. Churchalin et al., Clinical Immunosorbents Basing On Space-Network Polymers, 1998, pp. 1524-1529, All Union Research Institute of Chemical Reagents and Chemicals of Special Purity, Moscow.

P. De Deyne et al., Some Effects of Gamma Irradiation on Patellar Tendon Allografts, 1991, pp. 51-62, Connective Tissue Research, vol. 27.

R.I. Vaida et al., Structural-Functional Peculiarities of Myocardial Capillaries After Resection of the Lungs, Oct. 21, 1986, pp. 68-73.

R. Guidoin et al., A Compound Arterial Prosthesis: The Importance of the Sterilization Procedure on the Healing and Stability of Albuminated Polyester Grafts, Mar. 1985, pp. 122-128, Biomaterials, vol. 6.

Ph. Hernigou et al., Radiation Sterilization of Bone and the HIV Virus, 1993, pp. 445-451, Revue de Chirurgie Orthopedique, vol. 79.

Hsing-Wen Sung et al., Effects of Various Chemical Sterilization Methods on the Crosslinking and Enzymatic Degradation Characteristics of an Epoxy-Fixed Biological Tissue, Dec. 1996, pp. 376-383, Sterilization of Biological Tissues.

James R. Malm et al., Evaluation of Aortic Valve Homografts Sterilized by Electron Beam Energy, Oct. 1967, pp. 471-477, Journal of Thoracic and Cardiovascular Surgery, vol. 54, No. 4.

James R. Malm et al., Results of Aortic Valve Replacement Utilizing Irradiated Valve Homografts, pp. 740-747, Annals New York Academy of Sciences.

W. Oh et al., Mitral Valve Replacement With Preserved Cadaveric Aortic Homografts, May 1973, pp. 712-721, The Journal of Thoracic and Cardiovascular Surgery, vol. 65, No. 5.

K. Pietrucha, New Collagen Implant As Dural Substitue, Apr. 1991, pp. 320-323, Biomaterials, vol. 12.

Maria Raptopoulou-Gigi et al., Antimicrobial Proteins in Sterilised Human Milk, Jan. 1, 1977, pp. 12-14, British Medical Journal, vol. 1.

Edward A. Rittenhouse et al., Sterilization of Aortic Valve Grafts for Transplantation, Jul. 1970, pp. 1-5, Aortic Valve Grafts for Transplantation, Archives of Surgery, vol. 101, No. 1.

H. Sato et al., Sterilization of Therapeutic Immunoadsorbents by Ionizing Radiation, 1986, pp. 131-136, The International Journal of Artificial Organs, vol. 9, No. 2.

Richard A. Smith et al., Gamma Irradiation of HIV-1, 2001, pp. 815-819, Journal of Orthopaedic Research, vol. 19.

Barbara Lüssi-Schlatter et al., Die Antimikrobielle Behandlung von Peroralen Enzympräparaten mit Gamma-Strahlen, Pharmazeutisches Institut der Eidgenössischen Technischen Hochschule Zürich Galenische Abteilung.

Martindale's Extra Pharmacopoecia, Glucose p. 1265; prior art The Merck Index, Eleventh Edition Glucose pp. 4353-4354, prior art.

G.L. Moore et al., Effects of 4000 Rad. Irradiation on the In Vitro Storage Properties of packed Red Cells, Nov.-Dec. 1985, pp. 583-585, Final Rept., Pub. In Transfusion, vol. 25, No. 6 (Abstract).

Shcheglova et al., The Effect of the Power of Gamma-Radiation on the Radiation Dose in the Sterilization of Drugs, 1984, pp. 730-732, Khim-Farm Zh, vol. 18, No. 6 (Abstract).

G.A. Yarygina, Dose Rate Effect on Survival of Microorganisms Used As Test-Cultures in Radiation Sterilization of Medical Products, 1973, pp. 32-39, Radiats. Tekh., No. 9 (Abstract).

O. Cornu et al., Effect of Freeze-Drying and Gamma Irradiation on the Mechanical Properties of Human Cancellous Bone, 2000, pp. 426-431, Journal of Orthopaedic Research, vol. 18.

Anna Dziedzic-Goclawska et al., Effect of Radiation Sterilization on the Osteoinductive Properties and the Rate of Remodeling of Bone Implants Preserved by Lyophilization and Deep-Freezing, Nov. 1991, pp. 30-37, Clinical Orthopaedics and Related Research, vol. 272.

Ole T. Jensen et al., Vertical Guided Bone-Graft Augmentation in a New Canine Mandibular Model, Nov. 3, 1995, pp. 335-343, The International Journal of Oral and Maxillofacial Implants, vol. 10.

Ronald W. Katz et al., Radiation-Sterilized Insoluble Collagenous Bone Matrix is a Functional Carrier of Osteogenin for Bone Induction, 1990, pp. 183-185, Calcified Tissue International, vol. 47.

Everard Munting et al., Effect of Sterilization on Osteoinduction, 1988, pp. 34-38, Acta Orthop Scand, vol. 59, No. 1.

P.A. Puolakkainen et al., The effect of Sterilization on Transforming Growth Factor β Isolated From Demineralized Human Bone, 1993, pp. 679-685, Transfusion, vol. 33, No. 8.

U. Ripamonti et al., Long-Term Evaluation of Bone Formation by Osteogenic Protein 1 in the Baboon and Relative Efficacy of Bone-Derived Bone Morphogenetic Proteins Delivered by irradiated Xenogeneic Collagenous Matrices, 2000, pp. 1798-1809, Journal of Bone and Mineral Research, vol. 15, No. 9.

A. Salehpour et al., Dose-Dependent Response of Gamma Irradiation on Mechanical Properties and Related Biochemical Composition of Goat Bone-Patellar Tendon-Bone Allografts, 1995, pp. 898-906, The Journal of Orthopaedic Research, vol. 13.

Nikolaus Schwarz et al., Irradiation-sterilization of Rat Bone Matrix Gelatin, 1988, pp. 165-167, Acta Orthop Scand, vol. 59, No. 2.

C.W. Smith et al., Mechanical Properties of Tendons: Changes With Sterilization and Preservation, Feb. 1996, pp. 56-61, Journal of Biomechanical Engineering, vol. 118.

Yukiyoshi Toritsuka et al., Effect of Freeze-Drying or γ-Irradiation on Remodeling of Tendon Allograft in a Rat Model, 1997, pp. 294-300, Journal of Orthopaedic Research, vol. 15.

Konrad Wangerin et al., Behavior of Differently Sterilized Allogenic Lyophilized Cartilage Implants in Dogs, 1987, pp. 236-242, J. Oral Maxillofac Surg, vol. 45.

S. Wientroub et al., Influence of Irradiation on the Osteoinductive Potential of Demineralized Bone Matrix, 1988, pp. 255-260, Calcified Tissue International, vol. 42.

Alper, T. et al., Protection by Anoxia of the Scrapie Agent and some DNA and RNA Viruses Irradiated as Dry Preparations, J. Gen. Virol., 3:157-166 (1968).

Alper, T. et al., Does the Agent of Scrapie Replicate Without Nucleic Acid?, Nature, 214:764-766 (1967).

Alper, T. et al., The Scrapie Agent: Evidence Against its Dependence For Replication on Intrinsic Nucleic Acid, J. Gen. Virol., 41:503-516 (1978).

Blanchy, B.B. et al., Immobilization of Factor VIII on Collagen Membranes, J. Biomedical Materials Research, 20:469-479 (1986) (John Wiley & Sons, Inc.).

Borisova, E.A. et al., Protein Degradation During Interphase Death of Thymocytes Induced by Radation and Dexamethasone, pp. 519-521 (1990).

Boyer, T. D. et al., Radiation Inactivation of Microsomal Glutathione S-Transferase, The Journal of Biological Chemistry, 261:16963-16968 (1986).

Chanderkar, L.P. et al., The Involvement of Aromatic Amino Acids in Biological Activity of Bovine Fibrinogen as Assessed by Gamma-Irradiation, Radiation Research, 65:283-291 (1976) (Academic Press, Inc.).

Chanderkar, L.P. et al., Radiation-Induced Changes In Purified Prothrombin and Thrombin, Biochimica et Biophysica Acta, 706:1-8 (1982) (Elsevier Biomedical Press).

Chin, S. et al., Virucidal Treatment of Blood Protein Products With UVC Radiation, Photochemistry and Photobiology, 65:432-435 (1997) (American Society for Photobiology).

Dyskin, E.A. et al., Hemomicrocirculatory Bed in the Wall of Hollow Organs of the Dog Gastrointestinal Tract at Portal Hypertension, Arkh Anat Gistol Embiol, 93:58-68 (1987).

Ghosh, M.M. et al., A Comparison of Methodologies for the Preparation of Human Epidermal-Dermal Composites, Annals of Plastic Surgery; 39:390-404 (1997) (Lippincott-Raven Publishers).

Hsiue, G. et al., Absorbable Sandwich-Like Membrane for Retinal-Sheet Transplantation, pp. 20-25 (2002) (Wiley Periodicals, Inc).

Jensen, J. et al., Membrane-bound Na, K-ATPase: Target Size and Radiation Inactivation Size of Some of Its Enaymatic Reactions, J. Biological Chemistry, 263:18063-18070 (1988) (Am. Soc. for Biochem. and Mol. Biol.).

Kamat, H.N. et al., Correlation of Structural Alterations in Bovine Fibrinogen with Loss of Clotting Properties After Gamma Irradiation, Radiation Research, 49:381-389 (1972) (Academic Press, Inc.).

Kempner, E.S. et al., Effect of Environmental Conditions on Radiation Target Size Analyses, Analytical Biochemistry, 216:451-455 (1994).

Kempner, E.S. et al., Radiation-Damaged Tyrosinase Molecules are Inactive, Biophysical Journal, 55:159-162 (1989) (Biophysical Society).

Kuijpers, A.J. et al., In vivo Compatibility and Degradation of Crosslinked Gelatin Gels Incorporated in Knitted Dacron, pp. 137-144 (2000) (John Wiley & Sons, Inc.).

Le Maire, M. et al., Effects of Ionizing Radiations on Proteins, Journal of Biochem., 267:431-439 (1990).

Ma, J.T. et al., Functional Size Analysis of F-ATPase from *Escherichia coli* by Radiation Inactivation, The Journal of Biological Chemistry, 268:10802-10807 (1993) (The Am. Soc. for Biochem. and Mol. Bio., Inc.).

Marx, G. Protecting Fibrinogen with Rutin During UVC Irradiation for Viral Inactivation, Photochemistry and Photobiology, 63:541-546 (1996) (American Society for Photobiology).

Nagrani, S. et al., The Radiation-Induced Inactivation of External Yeast Invertase in Dilute Aqueous Solution, Int. J. Radiat. Biol., 55:191-200 (1989) (Taylor & Francis Ltd.).

Nielsen, M. et al., The Apparent Target Size of Rat Brain Benzodiazepine Receptor, Acetylcholinesterase, and Pyruvate Kinase Is Highly Influenced by Experimental Conditions, The Journal of Biological Chemistry, 263:11900-11906 (1988) (The American Society for Biochemistry and Molecular Biology, Inc.).

Plavsic, Z. M. et al., Resistance of Porcine Circovirus to Gamma Irradation, BioPharm, pp. 32-36 (Apr. 2001).

Potier, M. et al., Radiation Inactivation of Proteins: Temperature-Dependent Inter-Protomeric Energy Transfer in Ox Liver Catalase, Biochem. J., 298:571-574 (1994).

Sakai, T. et al., Microbiological Studies on Drugs and Their Raw Materials. IV. Sterilization of Microbial Contaminants in Enzyme Powder by Gamma Irradiation, Chem. Pharm. Bull., 26:1130-1134 (1978).

Salim-Hanna, M. et al., Free Radical Scavenging Activity Of Carnosine, Free Rad. Res. Comms., 14:263-270 (1991) (Harwood Academic Publishers GmbH).

Song, K.B. et al., Effect of Gamma-irradiation on the Physicochemical Properties of Blood Plasma Proteins, 2002 Annual Meeting and Food Expo-Anaheim, California, Session 30C-1, Food and Chemistry: Proteins, (Jun. 2002) (Abstract).

Suomela, H., Inactivation of Viruses in Blood and Plasma Products, Transfusion Medicine Reviews, 7:42-57 (1993) (W.B. Saunders Company).

(Abstract of EP0919198A2 and EP0919198A3 (Delphion-DERABS Abstact #G1999-304614)).

Website: www.wslfweb.org/docs/dstp2000.stopdf/19-MD.pdf, (Defense Science and Technology Plans, (Feb. 2000) p. 176, Section II, MD.03, U.S. Department of Defense Deputy Under Secretary of Defense (Science and Technology)).

Website: www.usacc.org/attaccc/ppt.html, (Advanced Technology Applications for Combat Casualty Care, 2001 Presentations, US Army Medical Research and Material Command Combat Casualty Care Research Program (2001)).

Website: www.usacc.org/RevisedStepB.html, Bakaltcheva, I. et al., (FY01 Request for Proposals-Intramural-Revised 2, Combat Casualty Care Research Program, (2000)).

Website: www.benvue.com/history/history_content.html, (2002).

Website: www.phase-technologies.com/html/vol.2no1.html, Jennings, T.A., (Glossary of Terms for Lyophilization) (1999).

Website: www.phase-technologies.com/html/vol.1no9.html, Jennings, T.A., (Overview of the Lypholization Process) (1998).

Website: www.phase-technologies.com/html/vol.1no2.html, Jennings, T.A., (Role of Product Temperature in the Lyophilization Process.

Website: www.phase-technologies.com/html/vol.2no2.html, Jennings, T.A., (What I Wish I Knew About Lyophilization) (1999).

Website: www.phase-technologies.com/html/vol.1no7.html, Jennings, T.A., (Which Shelf Temperature During Lyophilization?) (1998).

Website: www.phase-technologies.com/html/vol.1no10.html, Jennings, T.A., (Yes, You have no Eutectic) (1998).

Robert J. Woods, "Food Irradiation," Endeavor, New Series, vol. 18, No. 3, 1994, pp. 104-108.

A. Dziedzic-Goclawska et al., "Sterilisation of Tissue Allografts," Advances in Tissue Banking, vol. 1, pp. 261-321.

M.J. Goertzen et al., "Sterilisation of Canine Anterior Cruciate Allografts by Gamma Irradiation in Argon," Journal of Bone and Joint Surgery (Corrections), vol. 77-B, No. 2, Mar. 1995, pp. 205-212.

Robert J. Woods, "Food Irradiation," Endeavor, New Series, vol. 18, No. 3, 1994, pp. 104-108.

A. Dziedzic-Goclawska et al., "Sterilisation of Tissue Allografts," Advances in Tissue Banking, vol. 1, pp. 261-321.

M.J. Goertzen et al., "Sterilisation of Canine Anterior Cruciate Allografts by Gamma Irradiation in Argon," Journal of Bone and Joint Surgery (Corrections), vol. 77-B, No. 2, Mar. 1995, pp. 205-212.

P.V. Kapanin et al., "Feasibility of liposome cryoradiation sterilization," Khimiko-Farmatsevticheskii Zhurnal, 1988, vol. 22(4), Abstract, pp. 479-482.

* cited by examiner

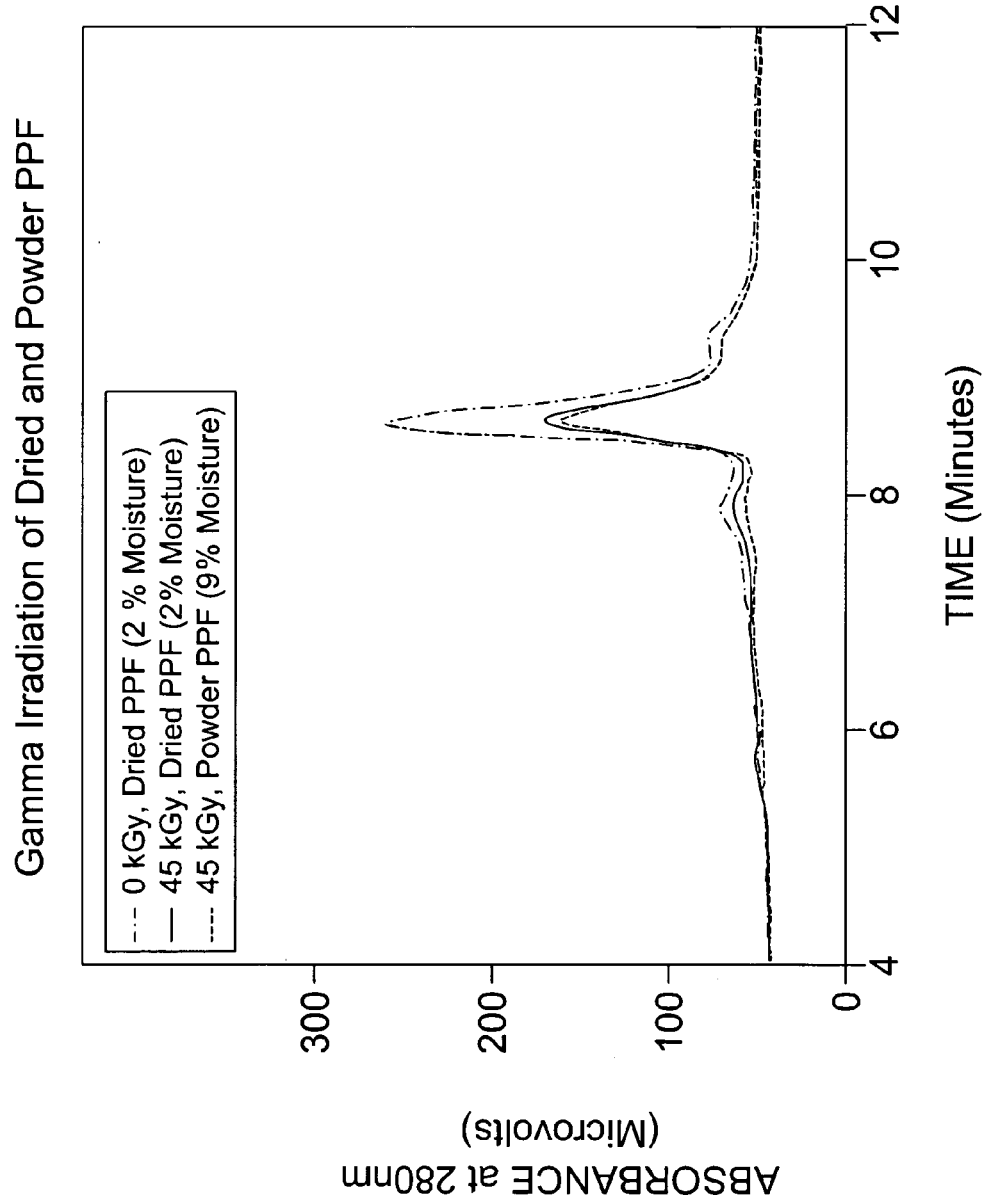

25% Albumin - Non-Reduced 1 2 3 4 5 6 7 8 9 10 11 12

| Std Kd | Lane | Sample |
|---|---|---|
| 200 | 1 | Empty |
| 116 | 2 | Broad Range Std. (BioRad) |
| 97 | 3 | Empty |
| 66 | 4 | 0 Kgy (Control) Box 3C (+ Ar) |
| 45 | 5 | 18.0 Kgy (~0.91 Kgy/hr) Box 1 (+ Ar) |
| | 6 | 23.0 Kgy (~0.92 Kgy/hr) Box 2 (+ Ar) |
| 31 | 7 | 30.4 Kgy (~1.01 Kgy/hr) Box 3 (+ Ar) |
| 21.5 | 8 | 0 Kgy (Control) Box 3C (- Ar) |
| 14.4 | 9 | 18.0 Kgy (~0.91 Kgy/hr) Box 1 (- Ar) |
| | 10 | 23.0 Kgy (~0.92 Kgy/hr) Box 2 (- Ar) |
| | 11 | 30.4 Kgy (~1.01 Kgy/hr) Box 3 (- Ar) |
| | 12 | Empty |

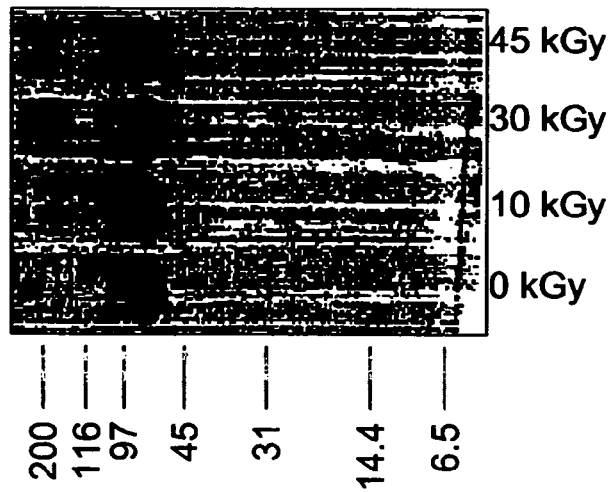

METHODS FOR STERILIZING PREPARATIONS CONTAINING ALBUMIN

FIELD OF THE INVENTION

The present invention relates to methods for sterilizing preparations containing albumin to reduce the level of one or more active biological contaminants or pathogens therein, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. The present invention particularly relates to methods of sterilizing preparations containing albumin, such as plasma protein fraction (PPF) products, with irradiation.

BACKGROUND OF THE INVENTION

Albumin is a highly soluble, ellipsoidal protein (MW 66,500), accounting for 70–80% of the colloid osmotic pressure of plasma. Accordingly, albumin is important in regulating the volume of circulating blood. When injected intravenously, 5% albumin will increase the circulating plasma volume by an amount approximately equal to the volume infused. This extra fluid reduces hemoconcentration and decreases blood viscosity. The degree and duration of volume expansion depend upon the initial blood volume. When treating patients with diminished blood volume, the effect of infused albumin may persist for many hours. In individuals with normal blood volumes, the hemodilution lasts for a much shorter time.

Albumin is also a transport protein and binds naturally occurring, therapeutic, and toxic materials in the circulation.

Albumin is distributed throughout the extracellular water and more than 60% of the body albumin pool is located in the extravascular fluid compartment. The total body albumin in a 70 kg man is approximately 350 g; it has a circulating life span of 15–20 days, with a turnover of approximately 15 g per day.

The minimum serum albumin level necessary to prevent or reverse peripheral edema is unknown. Although it undoubtedly varies from patient to patient, there is some evidence that it falls near 2.5 g per deciliter. This concentration provides a plasma oncotic pressure of 20 mm Hg (the equivalent of a total protein concentration of 5.2 g/dL).

Preparations containing albumin, including plasma protein fractions, are often provided therapeutically to humans and animals. For example, preparations containing albumin are frequently administered to humans for one or more of the following indications: hypovolemia, with or without shock; hypoalbumenimia, which may result from inadequate production of albumin (due to malnutrition, burns, major injury, congenital analbuminemia, liver disease, infection, malignancy, or endocrine disorders), excessive catabolism (due to burns, major injury, pancreatitis, thyrotoxicosis, pemphigus, or nephrosis), loss of albumin from the body (due to hemorrhage, excessive renal excretion, burn exudates, exudative enteropathy, or exfoliative dermatoses) and/or redistribution of albumin within the body (due to major surgery, cirrhosis with ascites, or various inflammatory conditions); prior to or during cardiopulmonary bypass surgery; and for the treatment of burns or cirrhosis.

A number of different preparations containing albumin for therapeutic use are or have been available commercially, including, for example, Albuminar® (Centeon/Aventis Behring), Buminate® (Baxter Laboratories), Plasbumin® (Bayer Biological), Albutein® (Alpha Therapeutic), Albumin (Human) (Immuno-U.S.), Albumarc® (American Red Cross) and Human Serum Albumin (Swiss Red Cross). Various plasma protein fraction products also are or have been available commercially, including, for example, Plasma-Plex® (Centeon/Aventis Behring), Protenate® (Baxter Laboratories), Plasmanate® (Bayer Biological) and Plasmatein® (Alpha Therapeutic).

Albumin is also used as a stabilizer in preparations of proteins, natural or recombinant, intended for therapeutic use. For example, albumin is presently found as a stabilizer in therapeutic preparations containing Factor VIII for hemophilia A (such as Recombinate® from Baxter-Hyland/Immuno), interferon beta-1b for multiple sclerosis (such as Betaseron® from Berlex Laboratories), erythropoietin for anemia (such as Epogen® from Amgen), alglucerase, a modified form of enzyme, β-glucocerebrosidase, for Gaucher's disease (such as Ceredase® from Genzyme) and antithrombin III for hereditary deficiency (such as Thrombate III® from Bayer or Atnativ® from Pharmacia & Upjohn). In such preparations, albumin may make up more than 99% of the total protein content.

Albumin is also found as a stabilizer in vaccine preparations, such as Tick-Born Encephalitis (TBE) Virus Vaccine and Measles, Mumps and Rubella Virus Vaccine Live (such as $MMR_{II}$® from Merck), Rabies Vaccine (such as RabAvert® from Chiron and Imovax® from Pasteur-Merieux) and Oral Polio Vaccine (such as Evans Polio Vaccine® from Evans/Medeva). In such preparations, albumin may again make up more than 99% of the total protein content.

Preparations containing albumin are also used as nutrient formulations in media for cell culture, including the culture of cells (recombinant or otherwise) producing desired products, and vaccine production. Such preparations are available commercially from, for example, Sigma-Aldrich, Irvine Scientific, Intergen and Valley Biomedical.

Many preparations containing albumin that are prepared for human, veterinary, diagnostic and/or experimental use may contain unwanted and potentially dangerous biological contaminants or pathogens, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. Consequently, it is of utmost importance that any biological contaminant or pathogen in the biological material be inactivated before the product is used. This is especially critical when the material is to be administered directly to a patient, for example in blood transfusions, blood factor replacement therapy, organ transplants and other forms of human therapy corrected or treated by intravenous, intramuscular or other forms of injection or introduction. This is also critical for the various biological materials that are prepared in media or via culture of cells or recombinant cells which contain various types of plasma and/or plasma derivatives or other biologic materials and which may be subject to mycoplasma, prion, bacterial, viral and other biological contaminants or pathogens.

Most procedures for producing biological materials have involved methods that screen or test the biological materials for one or more particular biological contaminants or pathogens rather than removal or inactivation of the contaminant(s) or pathogen(s) from the material. Materials that test positive for a biological contaminant or pathogen are merely not used. Examples of screening procedures include the testing for a particular virus in human blood from blood donors. Such procedures, however, are not always reliable and are not able to detect the presence of certain viruses, particularly in very low numbers. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the material is contaminated. Therefore, it would be desirable to apply techniques that would kill or inactivate contaminants or pathogens during and/or after manufacturing the biological material.

Moreover, to date, there is no reliable test or assay for identifying prions within a biological material that is suitable for screening out potential donors or infected material. This serves to heighten the need for an effective means of destroying priors within a biological material, while still retaining the desired activity of that material.

In conducting experiments to determine the ability of technologies to inactivate viruses, the actual viruses of concern are seldom utilized. This is a result of safety concerns for the workers conducting the tests, and the difficulty and expense associated with the containment facilities and waste disposal. In their place, model viruses of the same family and class are used.

In general, it is acknowledged that the most difficult viruses to inactivate are those with an outer shell made up of proteins, and that among these, the most difficult to inactivate are those of the smallest size. This has been shown to be true for gamma irradiation and most other forms of radiation as these viruses' diminutive size is associated with a small genome. The magnitude of direct effects of radiation upon a molecule are directly proportional to the size of the molecule, that is the larger the target molecule, the greater the effect. As a corollary, it has been shown for gamma-irradiation that the smaller the viral genome, the higher the radiation dose required to inactive it.

Among the viruses of concern for both human and animal-derived biological materials, the smallest, and thus most difficult to inactivate, belong to the family of Parvoviruses and the slightly larger protein-coated Hepatitis virus. In humans, the Parvovirus B19, and Hepatitis A are the agents of concern. In porcine-derived materials, the smallest corresponding virus is Porcine Parvovirus. Since this virus is harmless to humans, it is frequently chosen as a model virus for the human B19 Parvovirus. The demonstration of inactivation of this model parvovirus is considered adequate proof that the method employed will kill human B19 virus and Hepatitis A, and by extension, that it will also kill the larger and less hardy viruses such as HIV, CMV, Hepatitis B and C and others.

More recent efforts have focussed on methods to remove or inactivate contaminants in the products. Such methods include heat treating, filtration and the addition of chemical inactivants or sensitizers to the product.

Current standards of the U.S. Food and Drug Administration require that heat treatment of preparations containing albumin be heated to approximately 60° C. for a minimum of 10 hours, which can be damaging to sensitive biological materials. Indeed, heat inactivation can destroy 50% or more of the biological activity of certain biological materials.

Filtration involves filtering the product in order to physically remove contaminants. Unfortunately, this method may also remove products that have a high molecular weight. Further, in certain cases, small viruses may not be removed by the filter.

The procedure of chemical sensitization involves the addition of noxious agents which bind to the DNA/RNA of the virus and which are activated either by UV or other radiation. This radiation produces reactive intermediates and/or free radicals which bind to the DNA/RNA of the virus, break the chemical bonds in the backbone of the DNA/RNA, and/or cross-link or complex it in such a way that the virus can no longer replicate. This procedure requires that unbound sensitizer is washed from products since the sensitizers are toxic, if not mutagenic or carcinogenic, and cannot be administered to a patient.

Irradiating a product with gamma radiation is another method of sterilizing a product. Gamma radiation is effective in destroying viruses and bacteria when given in high total doses (Keathly et al., "Is There Life After Irradiation? Part 2," *BioPharm* July–August, 1993, and Leitman, Use of Blood Cell Irradiation in the Prevention of Post Transfusion Graft-vs-Host Disease," *Transfusion Science* 10:219–239 (1989)). The published literature in this area, however, teaches that gamma radiation can be damaging to radiation sensitive products, such as blood, blood products, protein and protein-containing products. In particular, it has been shown that high radiation doses are injurious to red cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective". Unfortunately, many sensitive biological materials, such as monoclonal antibodies (Mab), may lose viability and activity if subjected to freezing for irradiation purposes and then thawing prior to administration to a patient.

In view of the difficulties discussed above, there remains a need for methods of sterilizing preparations containing albumin that are effective for reducing the level of active biological contaminants or pathogens without an adverse effect on the preparation.

SUMMARY OF THE INVENTION

Accordingly, it is an object of the present invention to provide methods of sterilizing preparations containing albumin by reducing the level of active biological contaminants or pathogens without adversely effecting the preparation. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a method for sterilizing a preparation containing albumin that is sensitive to radiation comprising: (i) adding to a preparation containing albumin at least one stabilizer in an amount effective to protect the preparation containing albumin from radiation; and (ii) irradiating the preparation containing albumin with radiation at an effective rate for a time effective to sterilize the material.

Another embodiment of the present invention is directed to a method for sterilizing a preparation containing albumin that is sensitive to radiation comprising: (i) reducing the residual solvent content of a preparation containing albumin to a level effective to protect the preparation containing albumin from radiation; and (ii) irradiating the preparation containing albumin with radiation at an effective rate for a time effective to sterilize the preparation containing albumin.

Another embodiment of the present invention is directed to a method for sterilizing a preparation containing albumin that is sensitive to radiation comprising: (i) reducing the temperature of a preparation containing albumin to a level effective to protect the preparation containing albumin from radiation; and (ii) irradiating the preparation containing albumin with radiation at an effective rate for a time effective to sterilize the preparation containing albumin.

Another embodiment of the present invention is directed to a method for sterilizing a preparation containing albumin that is sensitive to radiation comprising: (i) applying to the preparation containing albumin a stabilizing process selected from the group consisting of: (a) reducing the residual solvent content of a preparation containing albumin, (b) adding to the preparation containing albumin at least one stabilizer, and (c) reducing the temperature of the preparation containing albumin; and (ii) irradiating the preparation containing albumin with radiation at an effective rate for a time effective to sterilize the preparation containing albumin, wherein the stabilizing process and the rate of irradiation are together effective to protect the preparation containing albumin from radiation.

Another embodiment of the present invention is directed to a method for sterilizing a preparation containing albumin that is sensitive to radiation comprising: (i) applying to the preparation containing albumin at least two stabilizing processes selected from the group consisting of: (a) reducing the residual solvent content of a preparation containing albumin, (b) adding to the preparation containing albumin at least one stabilizer, and (c) reducing the temperature of the preparation containing albumin; and (ii) irradiating the preparation containing albumin with radiation at an effective rate for a time effective to sterilize the preparation containing albumin, wherein the stabilizing processes may be performed in any order and are together effective to protect the preparation containing albumin from radiation.

The invention also provides a preparation containing albumin comprising albumin and a least one stabilizer in an amount effective to preserve the preparation for its intended use following sterilization with radiation.

The invention also provides a preparation containing albumin in which the residual solvent content has been reduced to a level effective to preserve the preparation for its intended use following sterilization with radiation.

The invention also provides a preparation containing albumin comprising albumin and at least one stabilizer in which the residual solvent content has been reduced and wherein the amount of stabilizer and level of residual solvent content are together effective to preserve the preparation for its intended use following sterilization with radiation.

The invention also provides a preparation containing albumin wherein the total protein concentration of the preparation is effective to preserve the preparation for its intended use following sterilization with radiation.

BRIEF DESCRIPTION OF THE DRAWINGS

FIGS. 1A, 1B and 1C show plasma protein fractions that were irradiated at varying levels of residual solvent content and in the presence or absence of volatile stabilizers.

FIGS. 6B–6C are gels showing the results of SDS-PAGE analysis of the irradiated plasma protein fractions.

DETAILED DESCRIPTION OF THE PREFERRED EMBODIMENTS

A. Definitions

Figure 1A:
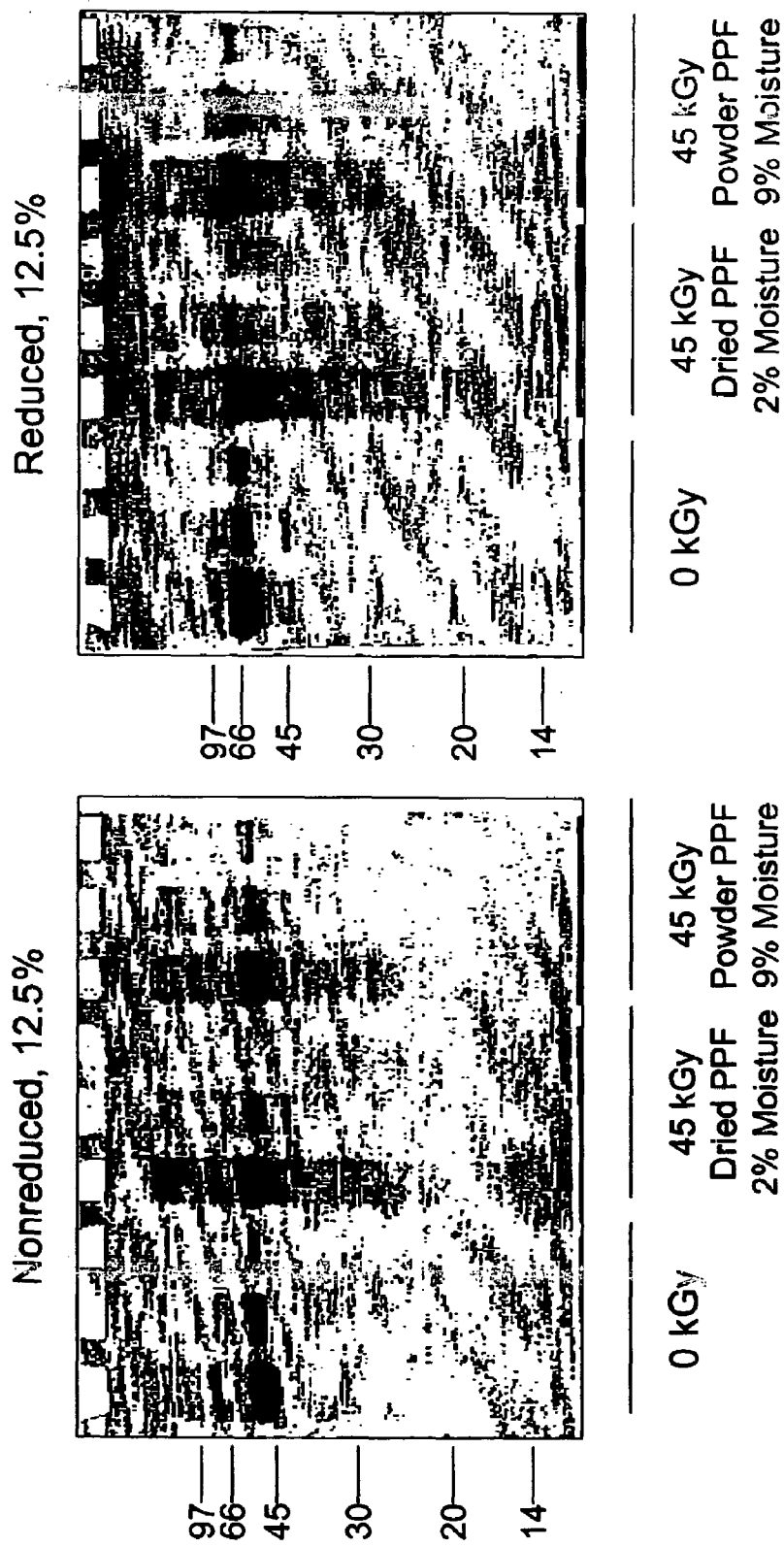

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "preparation containing albumin" is intended to mean any preparation derived or obtained from a living organism that contains the blood protein albumin, recombinant and transgenic, both native sequence and modified, or a variant or derivative thereof. Illustrative examples of preparations containing albumin include, but are not limited to, Albuminar® (Centeon/Aventis Behring), Buminate® (Baxter Laboratories), Plasbumin® (Bayer Biological), Albutein® (Alpha Therapeutic), Albumin (Human) (Immuno-U.S.) and Albumarc® (American Red Cross), and plasma protein fraction products, including, for example, Plasma-Plex® (Centeon/Aventis Behring), Protenate® (Baxter Laboratories), Plasmanate® (Bayer Biological) and Plasmatein® (Alpha Therapeutic).

As used herein, the term "sterilize" is intended to mean a reduction in the level of at least one active biological contaminant or pathogen found in the preparation containing albumin being treated according to the present invention.

As used herein, the term "biological material" is intended to mean any substance derived or obtained from a living organism. Illustrative examples of biological materials include, but are not limited to, the following: cells; tissues; blood or blood components; proteins, including recombinant and transgenic proteins, and proetinaceous materials; enzymes, including digestive enzymes, such as trypsin, chymotrypsin, alpha-galactosidase and iduronodate-2-sulfatase; immunoglobulins, including mono and polyimmunoglobulins; botanicals; food and the like. Preferred examples of biological materials include, but are not limited to, the following: ligaments; tendons; nerves; bone, including demineralized bone matrix, grafts, joints, femurs, femoral heads, etc.; teeth; skin grafts; bone marrow, including bone marrow cell suspensions, whole or processed; heart valves; cartilage; corneas; arteries and veins; organs, including organs for transplantation, such as hearts, livers, lungs, kidneys, intestines, pancreas, limbs and digits; lipids; carbohydrates; collagen, including native, afibrillar, atelomeric, soluble and insoluble, recombinant and transgenic, both native sequence and modified; chitin and its derivatives, including NO-carboxy chitosan (NOCC); stem cells, islet of Langerhans cells and other cells for transplantation, including genetically altered cells; red blood cells; white blood cells, including monocytes; and platelets.

As used herein, the term "biological contaminant or pathogen" is intended to mean a biological contaminant or pathogen that, upon direct or indirect contact with a preparation containing albumin, may have a deleterious effect on the preparation containing albumin or upon a recipient thereof. Such other biological contaminants or pathogens include the various viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites known to those of skill in the art to generally be found in or infect preparations containing albumin. Examples of other biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C and variants thereof), pox viruses, toga viruses, Ebstein-Barr viruses and parvoviruses; bacteria, such as *Escherichia, Bacillus, Campylobacter, Streptococcus* and *Staphalococcus*; nanobacteria; parasites, such as *Trypanosoma* and malarial parasites, including *Plasmodium* species; yeasts; molds; fungi; mycoplasmas and ureaplasmas; chlamydia; rickettsias, such as *Coxiella burnetti*; and prions and similar agents responsible, alone or in combination, for one or more of the disease states known as transmissible spongiform encephalopathies (TSEs) in mammals, such as scrapie, transmissible mink encephalopathy, chronic wasting disease (generally observed in mule deer and elk), feline spongiform encephalopathy, bovine spongiform encephalopathy (mad cow disease), Creutzfeld-Jakob disease (including variant CJD), Fatal Familial Insomnia, Gerstmann-Straeussler-Scheinker syndrome, kuru and Alpers syndrome. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in the preparation containing albumin and/or a recipient thereof.

As used herein, the term "blood components" is intended to mean one or more of the components that may be separated from whole blood and include, but are not limited to, the following: cellular blood components, such as red blood cells, white blood cells and platelets; blood proteins, such as blood clotting factors, enzymes, albumin, plasminogen, fibrinogen and immunoglobulins; and liquid blood components, such as plasma, plasma protein fraction (PPF), cryoprecipitate, plasma fractions and plasma-containing compositions.

As used herein, the term "cellular blood component" is intended to mean one or more of the components of whole blood that comprises cells, such as red blood cells, white blood cells, stem cells and platelets.

As used herein, the term "blood protein" is intended to mean one or more of the proteins that are normally found in whole blood. Illustrative examples of blood proteins found in mammals, including humans, include, but are not limited to, the following: coagulation proteins, both vitamin K-dependent, such as Factor VII and Factor IX, and non-vitamin K-dependent, such as Factor VIII and von Willebrands factor; albumin; lipoproteins, including high density lipoproteins and low density lipoproteins; complement proteins; globulins, such as immunoglobulins IgA, IgM, IgG and IgE; and the like. A preferred group of blood proteins includes Factor I (fibrinogen), Factor II (prothrombin), Factor III (tissue factor), Factor V (proaccelerin), Factor VI (accelerin), Factor VII (proconvertin, serum prothrombin conversion), Factor VIII (antihemophiliac factor A), Factor IX (antihemophiliac factor B), Factor X (Stuart-Prower factor), Factor XI (plasma thromboplastin antecedent), Factor XII (Hageman factor), Factor XIII (protransglutamidase), von Willebrands factor (vWF), Factor Ia, Factor IIa, Factor IIIa, Factor Va, Factor VIa, Factor VIIa, Factor VIIIa, Factor IXa, Factor Xa, Factor XIa, Factor XIIa and Factor XIIIa. Another preferred group of blood proteins includes proteins found inside red blood cells, such as hemoglobin and various growth factors, and derivatives of these proteins. Yet another preferred group of blood proteins include proteins found in commercially available plasma protein fraction products, such as Plasma-Plex® (Centeon/Aventis Behring), Protenate® (Baxter Laboratories), Plasmanate® (Bayer Biological) and Plasmatein® (Alpha Therapeutic).

As used herein, the term "liquid blood component" is intended to mean one or more of the fluid, non-cellular components of whole blood, such as plasma (the fluid, non-cellular portion of the whole blood of humans or animals as found prior to coagulation) and serum (the fluid, non-cellular portion of the whole blood of humans or animals as found after coagulation).

As used herein, the term "a biologically compatible solution" is intended to mean a solution to which a preparation containing albumin may be exposed, such as by being suspended or dissolved therein, and remain viable, i.e., retain its essential biological and physiological characteristics.

As used herein, the term "a biologically compatible buffered solution" is intended to mean a biologically compatible solution having a pH and osmotic properties (e.g., tonicity, osmolality and/or oncotic pressure) suitable for maintaining the integrity of the material(s) therein. Suitable biologically compatible buffered solutions typically have a pH between 4 and 8.5 and are isotonic or only moderately hypotonic or hypertonic. Biologically compatible buffered solutions are known and readily available to those of skill in the art.

As used herein, the term "stabilizer" is intended to mean a compound or material that reduces damage to the preparation containing albumin being irradiated to a level that is insufficient to preclude the safe and effective use of the material. Illustrative examples of stabilizers include, but are not limited to, the following: antioxidants; free radical scavengers, including spin traps; combination stabilizers, i.e. stabilizers which are effective at quenching both Type I and Type II photodynamic reactions; and ligands, such as heparin, that stabilize the molecules to which they bind. Preferred examples of stabilizers include, but are not limited to, the following: ethanol; acetone; fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tatranor-dihydrolipoic acid, furan fatty acids, oleic and linoleic and palmitic acids and their salts and derivatives; flavonoids, phenylpropaniods, and flavenols, such as quercetin, rutin and its derivatives, apigenin, aminoflavone, catechin, hesperidin and, naringin; carotenes, including beta-carotene; Co-Q10; xanthophylls; polyhydric alcohols, such as glycerol, mannitol; sugars, such as xylose, glucose, ribose, mannose, fructose and trehalose; amino acids and derivatives thereof, such as histidine, N-acetylcysteine (NAC), glutamic acid, tryptophan, sodium caprylate, N-acetyl tryptophan and methionine; azides, such as sodium azide; enzymes, such as Superoxide Dismutase (SOD) and Catalase; uric acid and its derivatives, such as 1,3-dimethyluric acid and dimethylthiourea; allopurinol; thiols, such as glutathione and reduced glutathione and cysteine; trace elements, such as selenium; vitamins, such as vitamin A, vitamin C (including its derivatives and salts such as sodium ascorbate and palmitoyl ascorbic acid) and vitamin E (and its derivatives and salts such as tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4,5-diol; reducing substances, such as butylated hydroxyanisole (BHA) and butylated hydroxytoluene (BHT); cholesterol; probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); proteins and peptides, such as glycylglycine and carnosine, in which each amino acid may be in its D or L form; diosmin; pupurogalin; gallic acid and its derivatives including but not limited to propyl gallate, sodium formaldehyde sulfoxylate and silymarin. Particularly preferred examples include single stabilizers or combinations of stabilizers that are effective at quenching both Type I and Type II photodynamic reactions and volatile stabilizers, which can be applied as a gas and/or easily removed by evaporation, low pressure and similar methods.

As used herein, the term "residual solvent content" is intended to mean the amount or proportion of freely-available liquid in the preparation containing albumin. Freely-available liquid means the liquid, such as water or an organic solvent (e.g. ethanol, isopropanol, acetone, polyethylene glycol, etc.), present in the preparation containing albumin being sterilized that is not bound to or complexed with one or more of the non-liquid components of the preparation containing albumin. Freely-available liquid includes intracellular water. The residual solvent contents related as water referenced herein refer to levels determined by the FDA approved, modified Karl Fischer method (Meyer and Boyd, *Analytical Chem.*, 31:215–219, 1959; May, et al., *J. Biol. Standardization*, 10:249–259, 1982; Centers for Biologics Evaluation and Research, FDA, Docket No. 89D-0140, 83–93; 1990) or by near infrared spectroscopy. Quantitation of the residual levels of other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viral, bacterial, prion and/or parasitic contaminants, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactines and their derivatives and analogs; angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphorins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide. In addition, atoms which bind to prions, and thereby increase their sensitivity to inactivation by radiation, may also be used. An illustrative example of such an atom would be the Copper ion, which binds to the prior protein and, with a Z number higher than the other atoms in the protein, increases the probability that the prion protein will absorb energy during irradiation, particularly gamma irradiation.

As used herein, the term "proteinaceous material" is intended to mean any material derived or obtained from a living organism that comprises at least one protein or peptide. A proteinaceous material may be a naturally occurring material, either in its native state or following processing/purification and/or derivatization, or an artificially produced material, produced by chemical synthesis or recombinant/transgenic technology and, optionally, process/purified and/or derivatized. Illustrative examples of proteinaceous materials include, but are not limited to, the following: proteins and peptides produced from cell culture; milk and other dairy products; ascites; hormones; growth factors; materials, including pharmaceuticals, extracted or isolated from animal tissue, such as heparin and insulin, or plant matter; plasma, including fresh, frozen and freeze-dried, and plasma protein fraction; fibrinogen and derivatives thereof, fibrin, fibrin I, fibrin II, soluble fibrin and fibrin monomer, and/or fibrin sealant products; whole blood; protein C; protein S; alpha-1 anti-trypsin (alpha-i protease inhibitor); butyl-cholinesterase; anticoagulants, such as coumarin drugs (warfarin); streptokinase; tissue plasminogen activator (tPA); erythropoietin (EPO); urokinase; neupogen; anti-thrombin-3; alpha-glucosidase; (fetal) bovine serum/horse serum; meat; immunoglobulins, including anti-sera, monoclonal antibodies, polyclonal antibodies and genetically engineered or produced antibodies; albumin; alpha-globulins; beta-globulins; gamma-globulins; coagulation proteins; complement proteins; and interferons.

As used herein, the term "radiation" is intended to mean radiation of sufficient energy to sterilize at least some component of the irradiated preparation containing albumin. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves. Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "E-beam" irradiation that involves their production via a machine. Visible light, both mono- and polychromatic, is produced by machines and may, in practice, be combined with invisible light, such as infrared and UV, that is produced by the same machine or a different machine.

As used herein, the term "to protect" is intended to mean to reduce any damage to the preparation containing albumin being irradiated, that would otherwise result from the irradiation of that material, to a level that is insufficient to preclude the safe and effective use of the material following irradiation. In other words, a substance or process "protects" a preparation containing albumin from radiation if the presence of that substance or carrying out that process results in less damage to the material from irradiation than in the absence of that substance or process. Thus, preparation containing albumin may be used safely and effectively after irradiation in the presence of a substance or following performance of a process that "protects" the material, but could not be used safely and effectively after irradiation under identical conditions but in the absence of that substance or the performance of that process.

B. Particularly Preferred Embodiments

A first preferred embodiment of the present invention is directed to a method for sterilizing a preparation containing albumin that is sensitive to radiation comprising irradiating the preparation containing albumin with radiation for a time effective to sterilize the material at a rate effective to sterilize the material and to protect the material from radiation.

Another preferred embodiment of the present invention is directed to a method for sterilizing a preparation containing albumin that is sensitive to radiation comprising: (i) adding to a preparation containing albumin at least one stabilizer in an amount effective to protect the preparation containing albumin from radiation; and (ii) irradiating the preparation containing albumin with radiation at an effective rate for a time effective to sterilize the material.

Another preferred embodiment of the present invention is directed to a method for sterilizing a preparation containing albumin that is sensitive to radiation comprising: (i) reducing the residual solvent content of a preparation containing albumin to a level effective to protect the preparation containing albumin from radiation; and (ii) irradiating the preparation containing albumin with radiation at an effective rate for a time effective to sterilize the preparation containing albumin.

Another preferred embodiment of the present invention is directed to a method for sterilizing a preparation containing albumin that is sensitive to radiation comprising: (i) reducing the temperature of a preparation containing albumin to a level effective to protect the preparation containing albumin from radiation; and (ii) irradiating the preparation containing albumin with radiation at an effective rate for a time effective to sterilize the preparation containing albumin.

Another preferred embodiment of the present invention is directed to a method for sterilizing a preparation containing albumin that is sensitive to radiation comprising: (i) applying to the preparation containing albumin a stabilizing process selected from the group consisting of: (a) reducing the residual solvent content of a preparation containing albumin, (b) adding to the preparation containing albumin at least one stabilizer, and (c) reducing the temperature of the preparation containing albumin; and (ii) irradiating the preparation containing albumin with radiation at an effective rate for a time effective to sterilize the preparation containing albumin, wherein the stabilizing process and the rate of irradiation are together effective to protect the preparation containing albumin from radiation.

Another preferred embodiment of the present invention is directed to a method for sterilizing a preparation containing albumin that is sensitive to radiation comprising: (i) applying to the preparation containing albumin at least two stabilizing processes selected from the group consisting of: (a) reducing the residual solvent content of a preparation containing albumin, (b) adding to the preparation containing albumin at least one stabilizer, and (c) reducing the temperature of the preparation containing albumin; and (ii) irradiating the preparation containing albumin with radiation at an effective rate for a time effective to sterilize the preparation containing albumin, wherein the stabilizing processes may be performed in any order and are together effective to protect the preparation containing albumin from radiation.

According to certain methods of the present invention, a stabilizer is added prior to irradiation of the preparation containing albumin with radiation. This stabilizer is preferably added to the preparation containing albumin in an amount that is effective to protect the preparation containing albumin from the radiation. Suitable amounts of stabilizer may vary depending upon certain features of the particular method(s) of the present invention being employed, such as the particular stabilizer being used and/or the nature and characteristics of the particular preparation containing albumin being irradiated and/or its intended use, and can be determined empirically by one skilled in the art.

According to certain methods of the present invention, the residual solvent content of the preparation containing albumin is reduced prior to irradiation of the preparation containing albumin with radiation. The residual solvent content is preferably reduced to a level that is effective to protect the preparation containing albumin from the radiation. Suitable levels of residual solvent content may vary depending upon certain features of the particular method(s) of the present invention being employed, such as the nature and characteristics of the particular preparation containing albumin being irradiated and/or its intended use, and can be determined empirically by one skilled in the art. There may be preparations containing albumin for which it is desirable to maintain the residual solvent content to within a particular range, rather than a specific value.

When the solvent is water, and particularly when the preparation of one or more digestive enzymes is in a solid phase, the residual solvent content is generally less than about 15%, typically less than about 10%, more typically less than about 9%, even more typically less than about 8%, usually less than about 5%, preferably less than about 3.0%, more preferably less than about 2.0%, even more preferably less than about 1.0%, still more preferably less than about 0.5%, still even more preferably less than about 0.2% and most preferably less than about 0.08%.

The solvent may preferably be a non-aqueous solvent, more preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In certain embodiments of the present invention, the solvent may be a mixture of water and a non-aqueous solvent or solvents, such as ethanol and/or acetone. In such embodiments, the non-aqueous solvent(s) is preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In a preferred embodiment, when the residual solvent is water, the residual solvent content of a preparation containing albumin is reduced by dissolving or suspending the preparation containing albumin in a non-aqueous solvent that is capable of dissolving water. Preferably, such a non-aqueous solvent is not prone to the formation of free-radicals upon irradiation and has little or no dissolved oxygen or other gas(es) that is (are) prone to the formation of free-radicals upon irradiation.

When the preparation containing albumin is in a liquid phase, reducing the residual solvent content may be accomplished by any of a number of means, such as by increasing the solute concentration. In this manner, the concentration of protein in the preparation containing albumin dissolved within the solvent may be increased to generally at least about 0.5%, typically at least about 1%, usually at least about 5%, preferably at least about 10%, more preferably at least about 15%, even more preferably at least about 20%, still even more preferably at least about 25%, and most preferably at least about 50%.

In certain embodiments of the present invention, the residual solvent content of a particular preparation containing albumin may be found to lie within a range, rather than at a specific point. Such a range for the preferred residual solvent content of a particular preparation containing albumin may be determined empirically by one skilled in the art.

While not wishing to be bound by any theory of operability, it is believed that the reduction in residual solvent content reduces the degrees of freedom of the preparation containing albumin, reduces the number of targets for free radical generation and may restrict the solubility of these free radicals. Similar results might therefore be achieved by lowering the temperature of the preparation containing albumin below its eutectic point or below its freezing point, or by vitrification to likewise reduce the degrees of freedom of the preparation containing albumin. These results may permit the use of a higher rate and/or dose of radiation than might otherwise be acceptable. Thus, the methods described herein may be performed at any temperature that doesn't result in unacceptable damage to the preparation containing albumin, i.e., damage that would preclude the safe and effective use of the preparation containing albumin. Preferably, the methods described herein are performed at ambient temperature or below ambient temperature, such as below the eutectic point or freezing point of the preparation containing albumin being irradiated.

In accordance with the methods of the present invention, an "acceptable level" of damage may vary depending upon certain features of the particular method(s) of the present invention being employed, such as the nature and characteristics of the particular preparation containing albumin and/or dipeptide stabilizer being used, and/or the intended use of the preparation containing albumin being irradiated, and can be determined empirically by one skilled in the art. An "unacceptable level" of damage would therefore be a level of damage that would preclude the safe and effective use of the preparation containing albumin being sterilized. The particular level of damage in a given preparation containing albumin may be determined using any of the methods and techniques known to one skilled in the art.

The residual solvent content of the preparation containing albumin may be reduced by any of the methods and techniques known to those skilled in the art for reducing solvent from a preparation containing albumin without producing an unacceptable level of damage to the preparation containing albumin. Such methods include, but are not limited to, evaporation, concentration, centrifugal concentration, vitrification and spray-drying.

A particularly preferred method for reducing the residual solvent content of a preparation containing albumin is lyophilization.

Another particularly preferred method for reducing the residual solvent content of a preparation containing albumin is vitrification, which may be accomplished by any of the methods and techniques known to those skilled in the art, including the addition of solute and or additional solutes, such as sucrose, to raise the eutectic point of the preparation containing albumin, followed by a gradual application of reduced pressure to the preparation containing albumin in order to remove the residual solvent, such as water. The resulting glassy material will then have a reduced residual solvent content.

According to certain methods of the present invention, the preparation containing albumin to be sterilized may be immobilized upon a solid surface by any means known and available to one skilled in the art. For example, the preparation containing albumin to be sterilized may be present as a coating or surface on a biological or non-biological substrate.

The radiation employed in the methods of the present invention may be any radiation effective for the sterilization of the preparation containing albumin being treated. The radiation may be corpuscular, including E-beam radiation. Preferably the radiation is electromagnetic radiation, including x-rays, infrared, visible light, UV light and mixtures of various wavelengths of electromagnetic radiation. A particularly preferred form of radiation is gamma radiation.

According to the methods of the present invention, the preparation containing albumin is irradiated with the radiation at a rate effective for the sterilization of the preparation containing albumin, while not producing an unacceptable level of damage to that material. Suitable rates of irradiation may vary depending upon certain features of the methods of the present invention being employed, such as the nature and characteristics of the particular preparation containing albumin being irradiated, the particular form of radiation involved and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to the methods of the present invention, the rate of irradiation may be optimized to produce the most advantageous combination of product recovery and time required to complete the operation. Both low (≦3 kGy/hour) and high (>3 kGy/hour) rates may be utilized in the methods described herein to achieve such results. The rate of irradiation is preferably be selected to optimize the recovery of the preparation containing albumin while still sterilizing the preparation containing albumin. Although reducing the rate of irradiation may serve to decrease damage to the preparation containing albumin, it will also result in longer irradiation times being required to achieve a particular desired total dose. A higher dose rate may therefore be preferred in certain circumstances, such as to minimize logistical issues and costs, and may be possible when used in accordance with the methods described herein for protecting a preparation containing albumin from irradiation.

According to a particularly preferred embodiment of the present invention, the rate of irradiation is not more than about 3.0 kGy/hour, more preferably between about 0.1 kGy/hr and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr, more preferably at least about 6 kGy/hr, even more preferably at least about 16 kGy/hr, and even more preferably at least about 30 kGy/hr and most preferably at least about 45 kGy/hr or greater.

According to the methods of the present invention, the preparation containing albumin to be sterilized is irradiated with the radiation for a time effective for the sterilization of the preparation containing albumin. Combined with irradiation rate, the appropriate irradiation time results in the appropriate dose of irradiation being applied to the preparation containing albumin. Suitable irradiation times may vary depending upon the particular form and rate of radiation involved and/or the nature and characteristics of the particular preparation containing albumin being irradiated. Suitable irradiation times can be determined empirically by one skilled in the art.

According to the methods of the present invention, the preparation containing albumin to be sterilized is irradiated with radiation up to a total dose effective for the sterilization of the preparation containing albumin, while not producing an unacceptable level of damage to that material. Suitable total doses of radiation may vary depending upon certain features of the methods of the present invention being employed, such as the nature and characteristics of the particular preparation containing albumin being irradiated, the particular form of radiation involved and/or the particular biological contaminants or pathogens being inactivated. Suitable total doses of radiation can be determined empirically by one skilled in the art. Preferably, the total dose of radiation is at least 25 kGy, more preferably at least 45 kGy, even more preferably at least 75 kGy, and still more preferably at least 100 kGy or greater, such as 150 kGy or 200 kGy or greater.

The particular geometry of the preparation containing albumin being irradiated, such as the thickness and distance from the source of radiation, may be determined empirically by one skilled in the art.

According to certain methods of the present invention, an effective amount of at least one sensitizing compound may optionally be added to the preparation containing albumin prior to irradiation, for example to enhance the effect of the irradiation on the biological contaminant(s) or pathogen(s) therein, while employing the methods described herein to minimize the deleterious effects of irradiation upon the preparation containing albumin. Suitable sensitizers are known to those skilled in the art, and include psoralens and their derivatives and inactines and their derivatives.

According to the methods of the present invention, the irradiation of the preparation containing albumin may occur at any temperature that is not deleterious to the preparation containing albumin being sterilized. According to one preferred embodiment, the preparation containing albumin is irradiated at ambient temperature. According to an alternate preferred embodiment, the preparation containing albumin is irradiated at reduced temperature, i.e. a temperature below ambient temperature, such as 0° C., −20° C., −40° C., −60° C., −78° C. or −196° C. According to this embodiment of the present invention, the preparation containing albumin is preferably irradiated at or below the freezing or eutectic point of the preparation containing albumin. According to another alternate preferred embodiment, the preparation containing albumin is irradiated at elevated temperature, i.e. a temperature above ambient temperature, such as 37° C., 60° C., 72° C. or 80° C. While not wishing to be bound by any theory, the use of elevated temperature may enhance the effect of irradiation on the biological contaminant(s) or pathogen(s) and therefore allow the use of a lower total dose of radiation.

Most preferably, the irradiation of the preparation containing albumin occurs at a temperature that protects the preparation from radiation. Suitable temperatures can be determined empirically by one skilled in the art.

In certain embodiments of the present invention, the temperature at which irradiation is performed may be found to lie within a range, rather than at a specific point. Such a range for the preferred temperature for the irradiation of a particular preparation containing albumin may be determined empirically by one skilled in the art.

According to the methods of the present invention, the irradiation of the preparation containing albumin may occur at any pressure which is not deleterious to the preparation containing albumin being sterilized. According to one preferred embodiment, the preparation of one or more digestive enzymes is irradiated at elevated pressure. More preferably, the preparation containing albumin is irradiated at elevated pressure due to the application of sound waves or the use of a volatile. While not wishing to be bound by any theory, the use of elevated pressure may enhance the effect of irradiation on the biological contaminant(s) or pathogen(s) and/or enhance the protection afforded by one or more stabilizers, and therefore allow the use of a lower total dose of radiation. Suitable pressures can be determined empirically by one skilled in the art.

Generally, according to the methods of the present invention, the pH of the preparation containing albumin undergoing sterilization is about 7. In some embodiments of the present invention, however, the preparation containing albumin may have a pH of less than 7, preferably less than or equal to 6, more preferably less than or equal to 5, even more preferably less than or equal to 4, and most preferably less than or equal to 3. In alternative embodiments of the present invention, the preparation containing albumin may have a pH of greater than 7, preferably greater than or equal to 8, more preferably greater than or equal to 9, even more preferably greater than or equal to 10, and most preferably greater than or equal to 11. According to certain embodiments of the present invention, the pH of the preparation undergoing sterilization is at or near the isoelectric point of the enzyme(s) contained in the preparation. Suitable pH levels can be determined empirically by one skilled in the art.

Similarly, according to the methods of the present invention, the irradiation of the preparation containing albumin may occur under any atmosphere that is not deleterious to the preparation containing albumin being treated. According to one preferred embodiment, the preparation containing albumin is held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the preparation containing albumin is held under vacuum while being irradiated. According to a particularly preferred embodiment of the present invention, a preparation containing albumin (lyophilized, liquid or frozen) is stored under vacuum or an inert atmosphere (preferably a noble gas, such as helium or argon, more preferably a higher molecular weight noble gas, and most preferably argon) prior to irradiation. According to an alternative preferred embodiment of the present invention, a liquid preparation containing albumin is held under low pressure, to decrease the amount of gas, particularly oxygen, dissolved in the liquid, prior to irradiation, either with or without a prior step of solvent reduction, such as lyophilization. Such degassing may be performed using any of the methods known to one skilled in the art.

In another preferred embodiment, where the preparation containing albumin contains oxygen or other gases dissolved within or associated with it, the amount of these gases within or associated with the preparation may be reduced by any of the methods and techniques known and available to those skilled in the art, such as the controlled reduction of pressure within a container (rigid or flexible) holding the preparation to be treated or by placing the preparation in a container of approximately equal volume.

In certain embodiments of the present invention, when the preparation containing albumin to be treated is a tissue, at least one stabilizer is introduced according to any of the methods and techniques known and available to one skilled in the art, including soaking the tissue in a solution containing the stabilizer(s), preferably under pressure, at elevated temperature and/or in the presence of a penetration enhancer, such as dimethylsulfoxide. Other methods of introducing at least one stabilizer into a tissue include, but are not limited to, applying a gas containing the stabilizer(s), preferably under pressure and/or at elevated temperature, injection of the stabilizer(s) or a solution containing the stabilizer(s) directly into the tissue, placing the tissue under reduced pressure and then introducing a gas or solution containing the stabilizer(s) and combinations of two or more of these methods. One or more sensitizers may also be introduced into a tissue according to such methods.

It will be appreciated that the combination of one or more of the features described herein may be employed to further minimize undesirable effects upon the preparation containing albumin caused by irradiation, while maintaining adequate effectiveness of the irradiation process on the biological contaminant(s) or pathogen(s). For example, in addition to the use of a stabilizer, a particular preparation containing albumin may also be lyophilized, held at a reduced temperature and kept under vacuum prior to irradiation to further minimize undesirable effects.

The sensitivity of a particular biological contaminant or pathogen to radiation is commonly calculated by determining the dose necessary to inactivate or kill all but 37% of the agent in a sample, which is known as the $D_{37}$ value. The desirable components of a preparation containing albumin may also be considered to have a $D_{37}$ value equal to the dose of radiation required to eliminate all but 37% of their desirable biological and physiological characteristics.

In accordance with certain preferred methods of the present invention, the sterilization of a preparation containing albumin is conducted under conditions that result in a decrease in the $D_{37}$ value of the biological contaminant or pathogen without a concomitant decrease in the $D_{37}$ value of the preparation containing albumin. In accordance with other preferred methods of the present invention, the sterilization of a preparation containing albumin is conducted under conditions that result in an increase in the $D_{37}$ value of the preparation containing albumin. In accordance with the most preferred methods of the present invention, the sterilization of a preparation containing albumin is conducted under conditions that result in a decrease in the $D_{37}$ value of the biological contaminant or pathogen and a concomitant increase in the $D_{37}$ value of the preparation containing albumin.

EXAMPLES

The following examples are illustrative, but not limiting, of the present invention. Other suitable modifications and adaptations are of the variety normally encountered by those skilled in the art and are fully within the spirit and scope of the present invention. Unless otherwise noted, all irradiation was accomplished using a $^{60}$Co source.

Example 1

In this experiment, plasma protein fractions were irradiated (45 kGy at 1.9 kGy/hr at ambient temperature) at varying levels of residual solvent content and in the presence or absence of volatile stabilizers.

Method

In glass vials, samples of a commercially available plasma protein fraction (2 mg/ml) were prepared having either 9% water containing small amounts of ethanol and acetone or ~1% water containing substantially no ethanol or acetone. Samples were irradiated with gamma radiation (45 kGy total dose at 1.9 kGy/hr and ambient temperature) and then assayed for structural integrity. Structural integrity was determined by SDS-PAGE, HPLSEC and reverse phase HPLC.

For SDS-PAGE, three 12.5% gels were prepared according to the following recipe: 4.2 ml acrylamide; 2.5 ml 4X-Tris (pH 8.8); 3.3 ml water; 100 µl 10% APS solution; and 10 µl TEMED, and placed in an electrophoresis unit with 1× Running Buffer (15.1 g Tris base; 72.0 g glycine; 5.0 g SDS in 1 l water, diluted 5-fold). Irradiated and control samples (1 mg/ml) were diluted with Sample Buffer (+/− beta-ME) in Eppindorf tubes and then centrifuged for several minutes. 20 µl of each diluted sample (10 µg) were assayed.

For reverse phase HPLC, each sample was dissolved in water to a final concentration of 110 mg/ml. These solutions were then serially diluted into 0.1% trifluoroacetic acid to the desired concentration. 10 µg of each sample was loaded onto an Aquapore RP-300 (C-8) 2.1×30 mm Microbore HPLC: Applied Biosystems 130A Separation System, flow rate 0.2 ml/min. Solvent A: 0.1% trifluoroacetic acid; solvent B: 70% acetonitrile, 30% water, 0.085% trifluoroacetic acid.

For HPLSEC, each sample was diluted to 0.4 µg/µl and 50 µl thereof loaded onto a Phenomenex-Biosep S3000 (molecular range 5 kDa–700 kDa) for an analysis concentration of 20 µg: 20 µl of 2 mg/ml stock solution+80 µl elution buffer (50 mM $NaP_i$+100 mM NaCl pH 6.7); flow rate 1 ml/min Results Both samples exhibited some breakdown of albumin upon irradiation to 45 kGy, with the sample having 9% water containing small amounts of ethanol and acetone exhibiting less breakdown and greater structural recovery than the sample containing less water and substantially no volatile stabilizers. The structural recovery of both samples, however, was sufficient for subsequent use of the albumin.

Figure 1C:
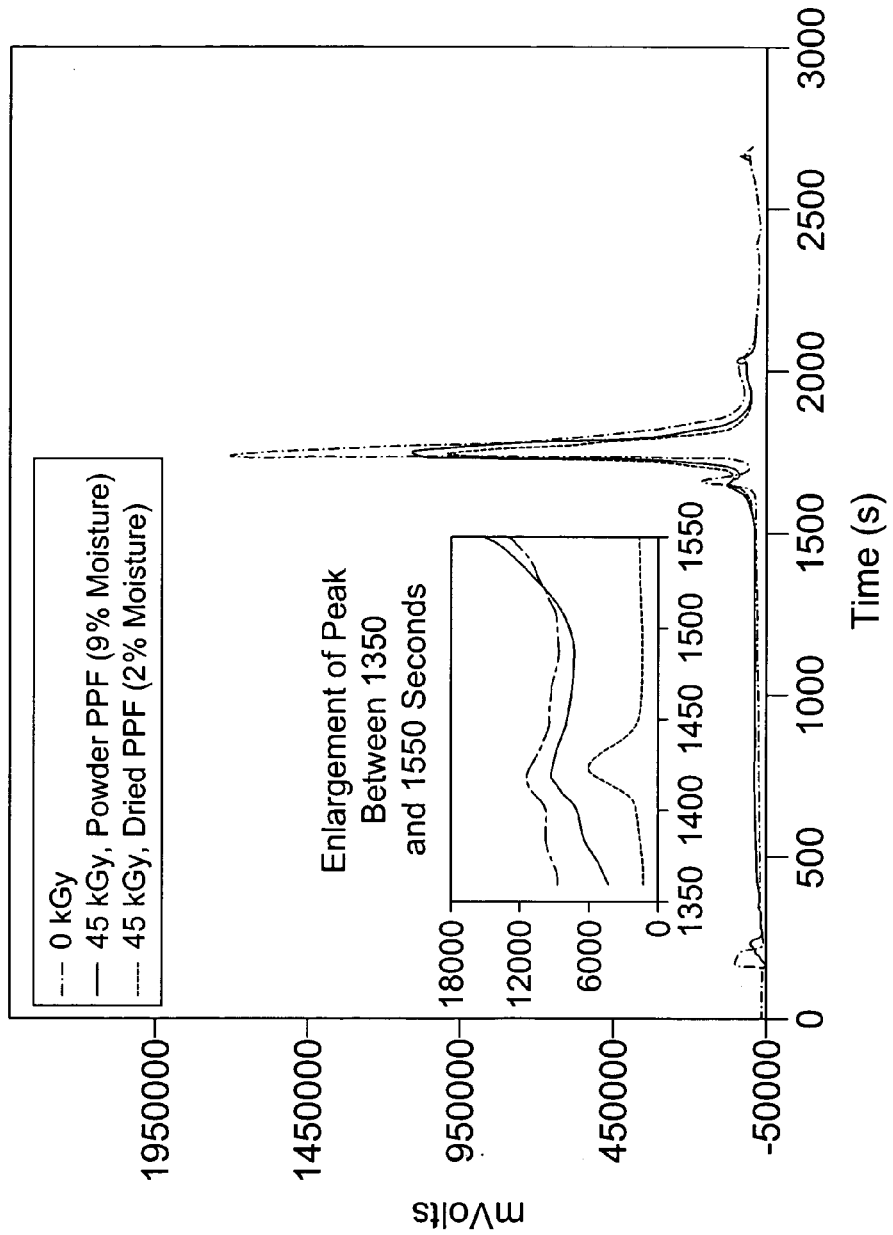
Figure 2A:
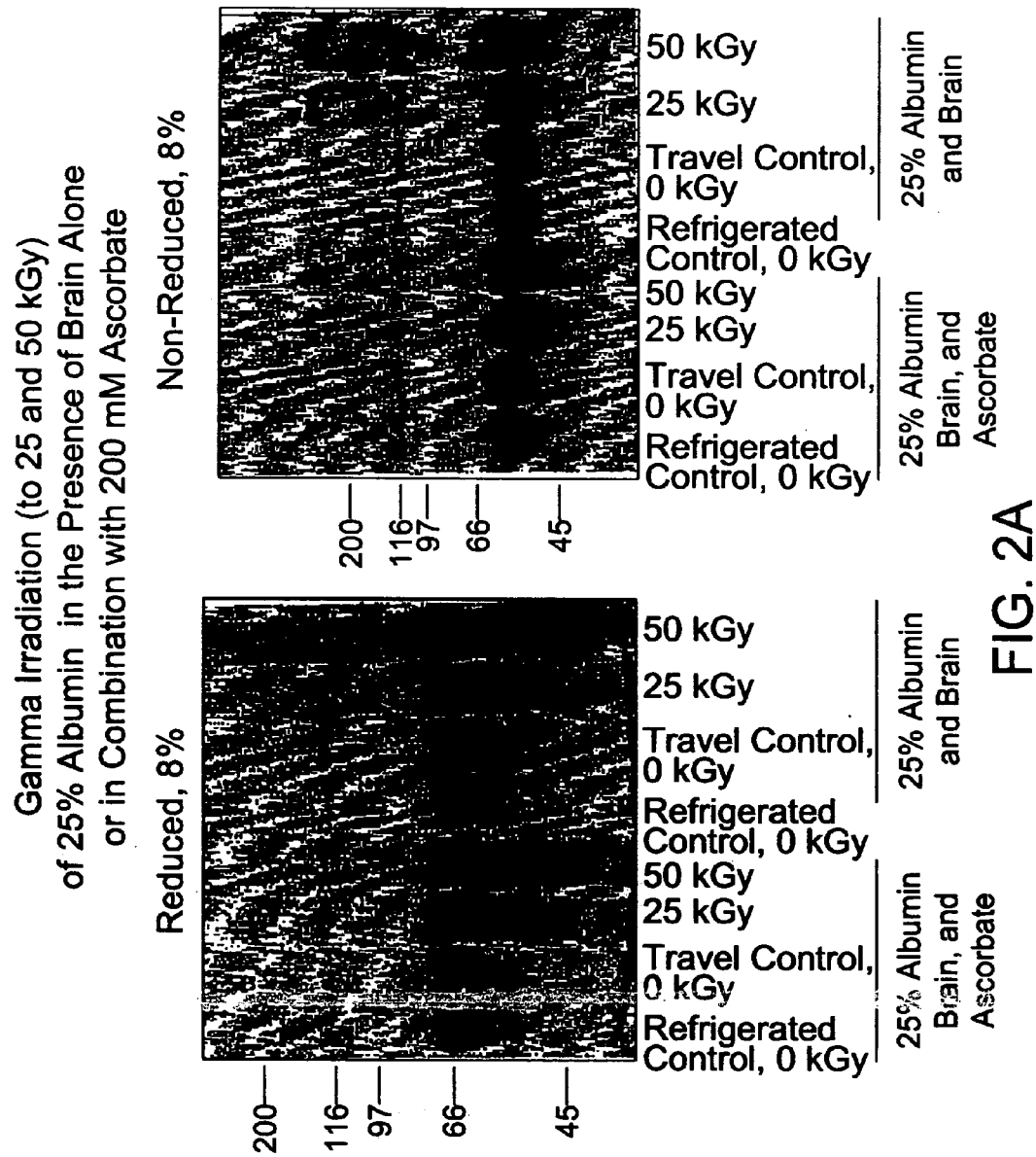
FIGS. 2A–2F show human albumin (25%) spiked 1:100 with 10% brain homogenate from hamster adapted scrapie (strain 263K) that was irradiated and assayed for scrapie infectivity.
Figure 2B:
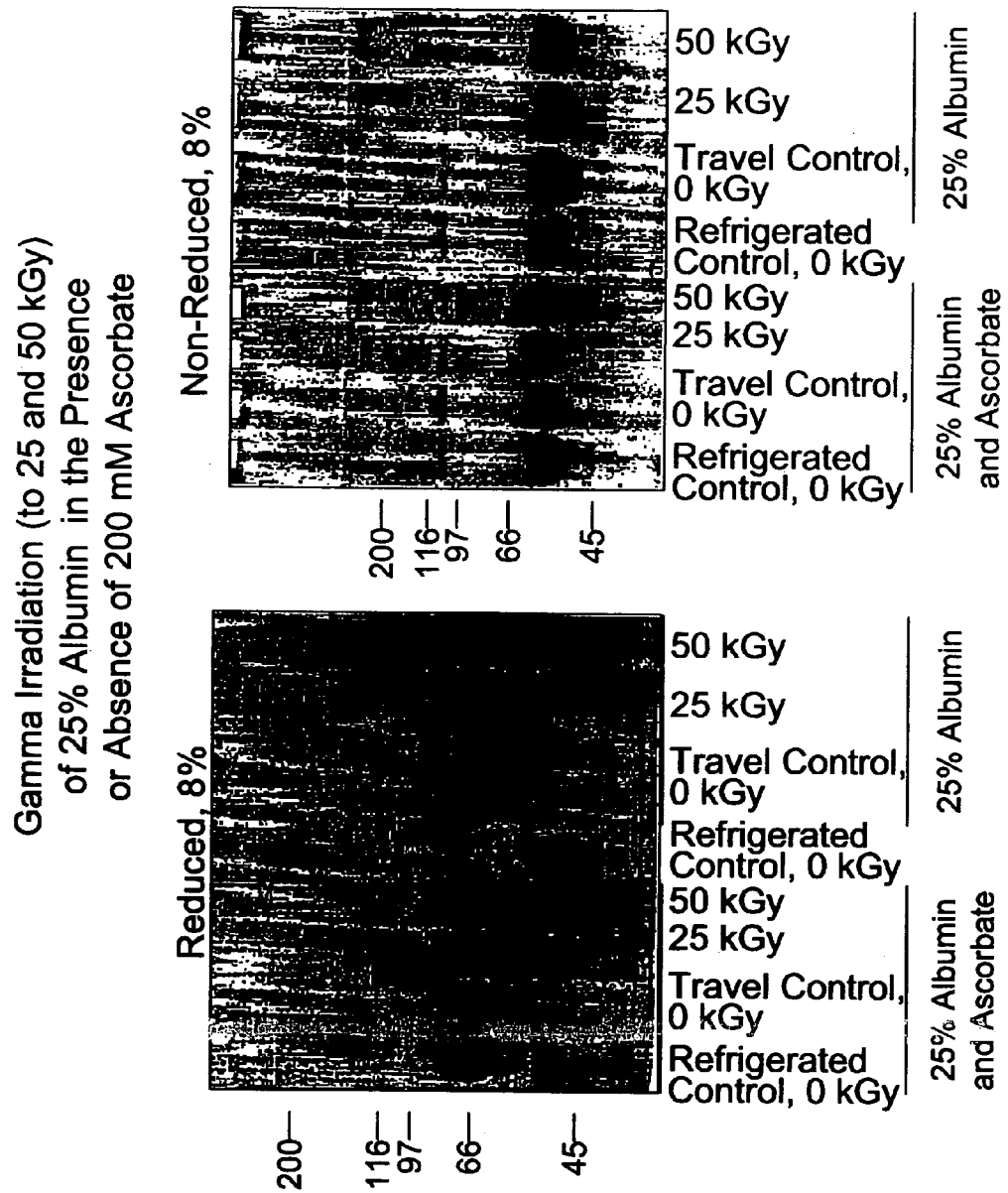
Figure 2C:
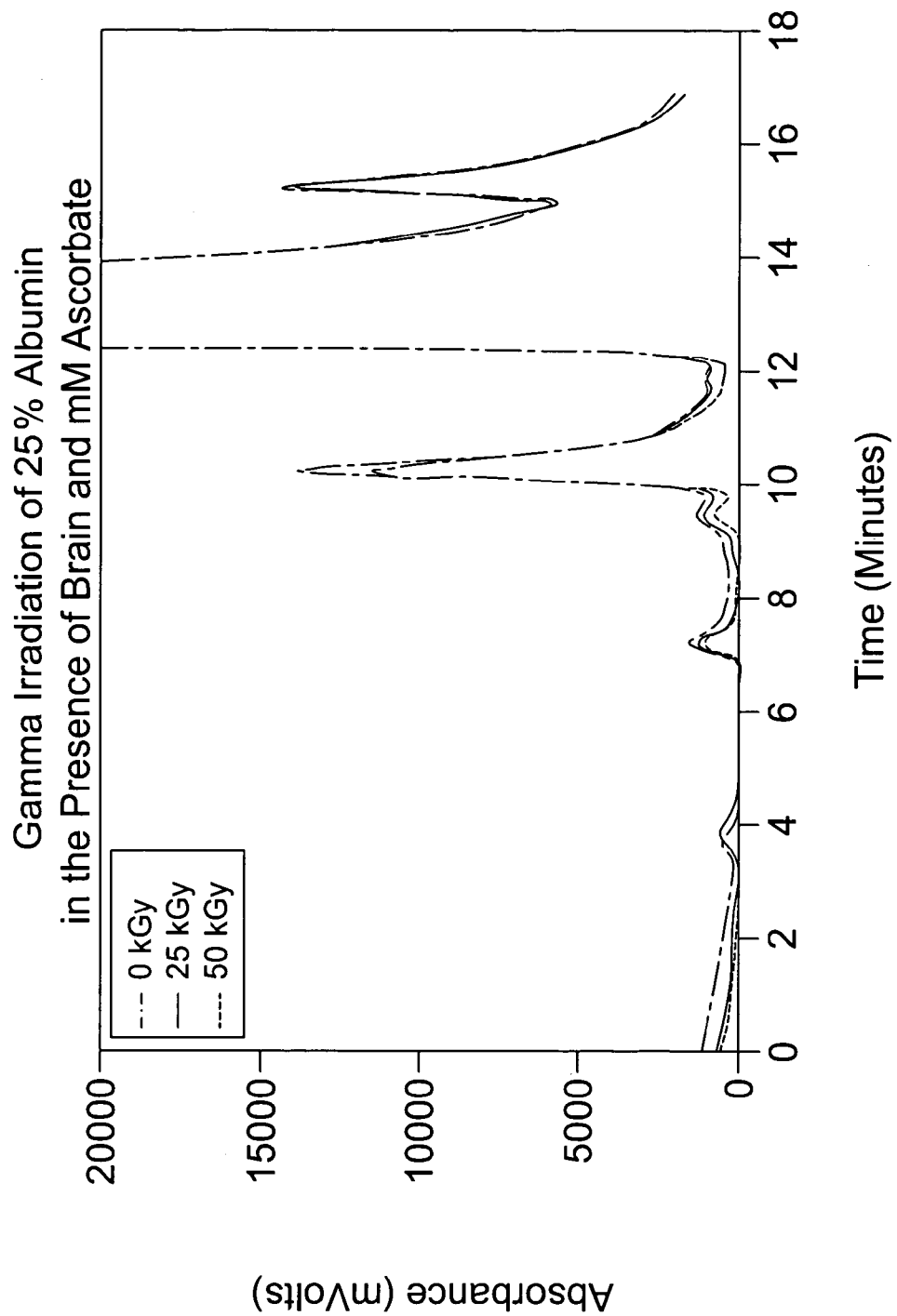
Figure 2D:
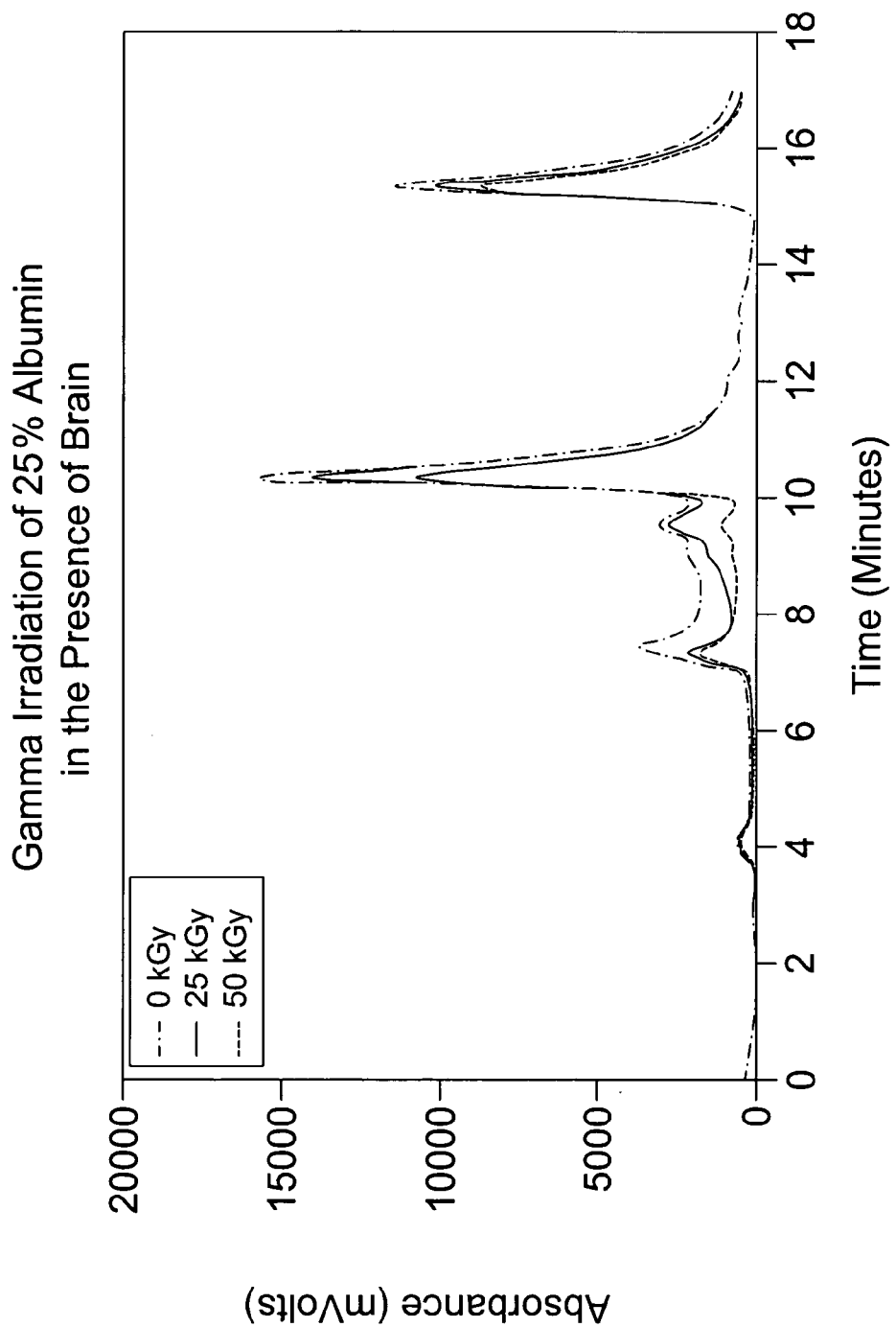
Figure 2E:
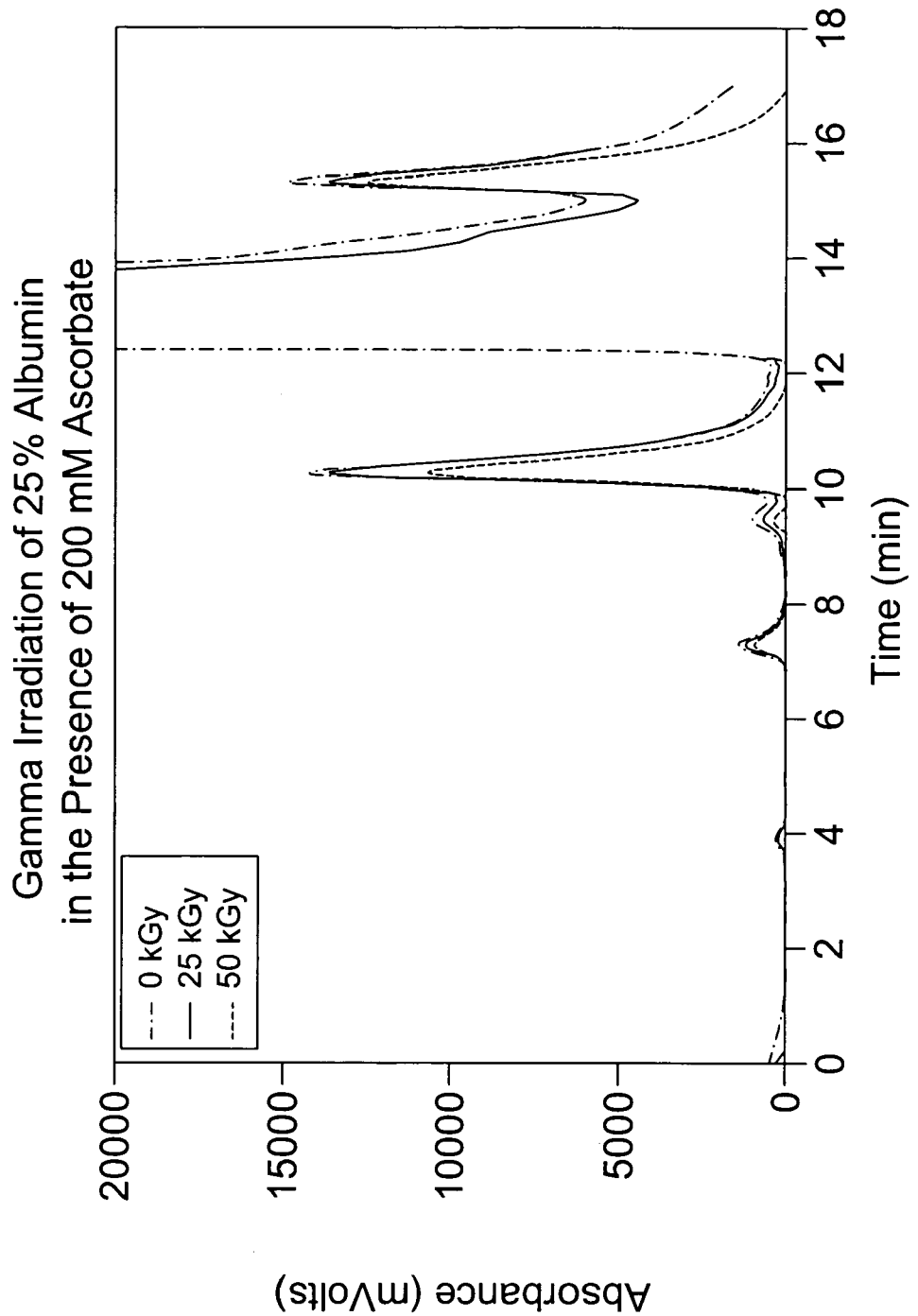
Figure 2F:
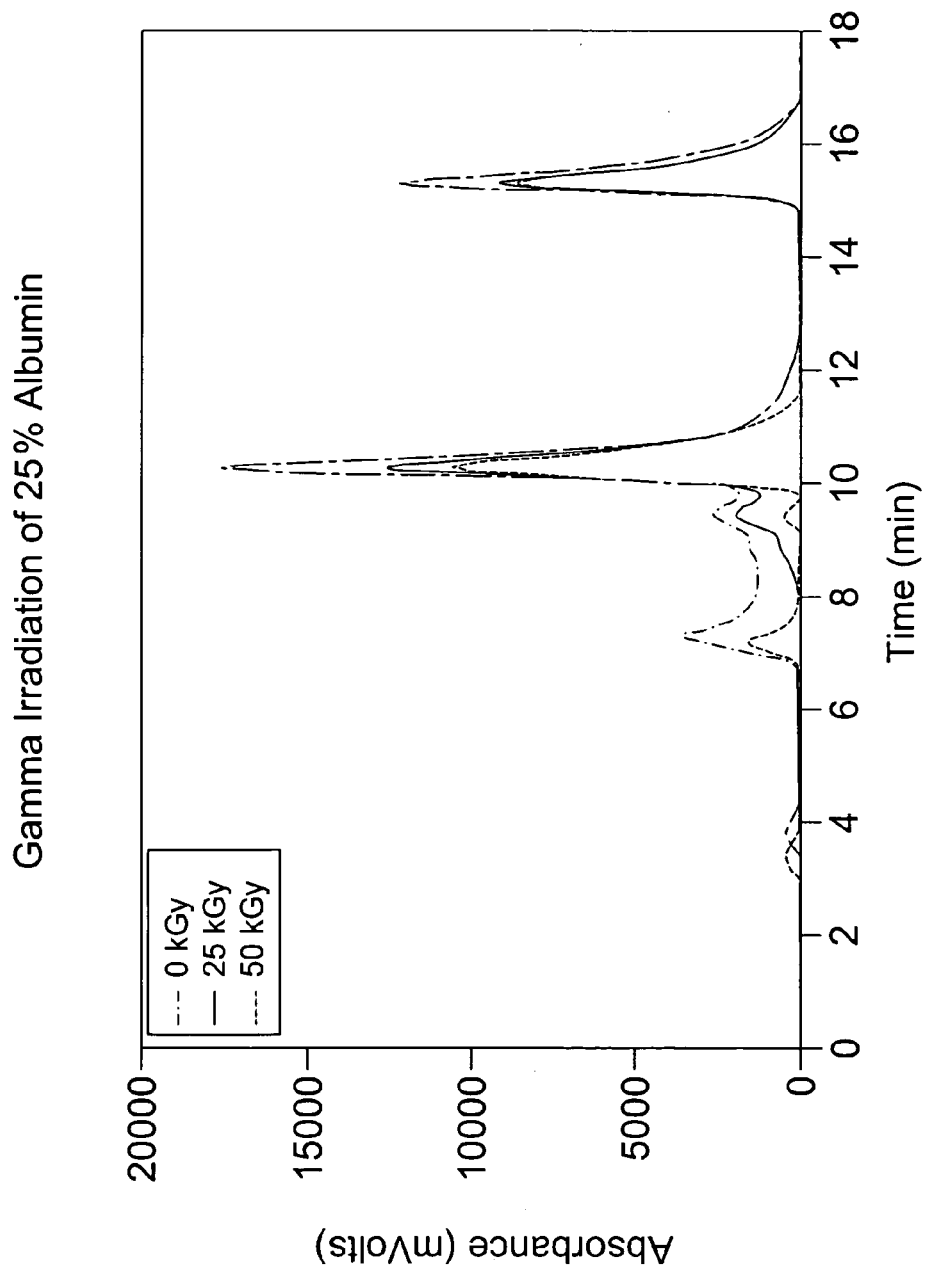

More specifically, as shown in FIG. 1A, SDS-PAGE analysis demonstrates better recovery of albumin monomer from the sample having 9% water containing small amounts of ethanol and acetone. Similarly, as shown in FIG. 1B, HPLSEC also indicates less aggregation in the sample having 9% water containing small amounts of ethanol and acetone. As shown in FIG. 1C, reverse phase HPLC showed no significant difference between irradiated samples and control.

Example 2

Human albumin (25%) was spiked 1:100 with 10% brain homogenate from hamster adapted scrapie (strain 263K). The sample was mixed by vortexing, and 4 6-ml aliquots of scrapie-spiked albumin were dispensed into 10-ml serum vials. One vial was stored at −80° C. as a frozen control. Three vials were taken to a commercial irradiation facility. One vial (the 0 kGy control) was refrigerated to prevent bacterial growth. The remaining vials were irradiated at ambient temperature (20–25° C.) at a rate of 0.4 kGy/hr to a total dose of 26 or 50 kGy. Radiation dose was assessed by dosimeters attached to each vial and by external dosimeters placed in close proximity to the vials. The irradiated samples and the 0 kGy control were assayed for scrapie infectivity.

Infectivity was assayed by intracerebral inoculation of 0.05 ml of sample into 12 hamsters, which were then held for up to 6 months for observation. Three clinical endpoints were assessed: wobble, failure-to-rear and death. There was an at least 8–10 day delay in the appearance of each clinical symptom in the group inoculated with the sample treated at the higher dose compared with the unirradiated control. The data were compared with a nomogram constructed from the dose response of the incubation time for a large number of animals infected in limiting dilution series mode (R. Rowher, unpublished data). This nomogram correlated days to onset of disease (as evidenced by wobble) with $\log_{10} LD_{50}$ inoculated.

The effect of the radiation on the biological material (albumin) was determined by SDS-PAGE gel electrophoresis and high performance size exclusion chromatography as follows.

SDS-PAGE was conducted in 8% polyacrylamide gels in a Mighty Small Mini-Vertical Unit SE250/SE260. Samples were diluted 1:100 in PBS and then 1:1 in Laemmli Sample Buffer (Bio-Rad) with or without 5% β-mercaptoethanol. Sample load was 12.5 μg per lane. The molecular weight markers were Low-Range Standard (Bio-Rad). Electrophoresis was conducted for 30 minutes at 125 volts. Gels were stained with 0.1% Coomassie Brilliant Blue R-250 in 50% methanol, 10% acetic acid and destained with 5% methanol, 9% acetic acid.

HPSEC was performed on 7.8×300 mm Biosep SEC columns (Phenomenex, Torrence, Calif.) in 130A Separation System (Applied Biosystems). The eluant buffer of 0.05M sodium phosphate, 0.1 M sodium chloride (pH 6.7) was filtered before use with 0.22 μm filters. Albumin solutions were diluted to a final concentration of 1.25 mg/ml in eluant buffer and 25 μl (31.25 μg protein) was injected. Flow rate was 1 ml/min. Detection was by absorbance at 280 nm.

Results

For the unirradiated control, the median incubation time for onset of disease (wobble) was 75 days. For the irradiated samples, the median incubation time for onset of disease was 88 days for the sample irradiated to a total dose of 25 kGy and 90 days for the sample irradiated to 50 kGy. Comparison with the nomogram gave estimated values for the $\log_{10}$ titers as 6.5 for the unirradiated control and 4.8 and 4.6 for the samples irradiated to 25 kGy and 50 kGy, respectively. Based on these estimates, the median reduction factors for the irradiated samples were 1.7 and 1.9 for the samples irradiated to 25 kGy and 50 kGy, respectively These represent estimates of the median reduction values, but do not convey the maximum possible reduction predicted by this experiment. To do this, the minimum value of the 95% confidence interval (CI) of the control group should be compared with the maximum value of the 95% CI of the radiation treated groups. This calculation will yield the maximum reduction factor of the titres that lies within the 95% CI. For the 50 kGy group this value was 3.5 logs reduction.

The susceptibility of biological contaminants or pathogens to radiation is often expressed as their $D_{37}$ value. This represents the dose of radiation required to reduce the number of active biological contaminants or pathogens to 37% of their pre-irradiation number. Thus the lower the $D_{37}$, the more susceptible a particular biological contaminant or pathogen is to the effects of the radiation. The $D_{37}$ of the scrapie prion has been determined experimentally to be approximately 47 kGy (Rohwer, *Nature,* 308, 5960, pp. 658–662, 1984). Utilizing the methodology described herein, the $D_{37}$ of the scrapie prion was unexpectedly found to be only 4.5 kGy. Thus the $D_{37}$ of the prion was decreased using the methods and formulation employed in this experiment. Thus increased destruction of the scrapie prion was achieved while maintaining the integrity of the biological material, a commercial therapeutic 25% solution of human albumin, used in this experiment.

Increased destruction of the scrapie prion was achieved while maintaining the essential biological and physiological characteristics of the preparation containing albumin being treated. This particular biological material, a 25% solution of human albumin, was examined both pre- and post-irradiation with gamma radiation to total doses of 25, 50 and 100 kGy. As shown by gel electrophoresis (FIGS. 2A–2B), the albumin was largely intact at radiation doses up to 50 kGy, with only a small amount of fragmentation and aggregation and a slight decrease in the amount of the monomeric form of albumin. The results were similar for all of the albumin samples, irrespective of whether they contained any ascorbate and/or hamster. At higher doses, minor changes were seen in the albumin samples, mostly in the form of an increased polymerization of albumin.

A more detailed analysis was made using HPSEC. As shown in FIGS. 2C–2F, with irradiation, the amount of albumin monomer decreased (peak at 10.5 min), the amount of dimer increased (9 min) and the amount of polymer increased (7.2 min). These changes were all minimized in the presence of ascorbate. The remaining peaks at 12.6 and 15.3 min are those of ascorbate and the N-acetyl tryptophan stabilizer, respectively.

Example 3

In the experiment, lyophilized albumin (containing 5% urokinase) was irradiated at a rate of 1.847 kGy/hr at approximately 4° C. to a total dose of 10 or 40 kGy.

Samples were analyzed by gel filtration using a TSKgel G4000SW$_{\mathit{xl}}$ 30 cm×7.8 mm column, separation range 20 kDa–7,000 kDa, elution buffer 0.1M sodium phosphate/ 0.1M sodium sulfate (pH 6.5), flow rate 1 ml/min.

Figure 3A:
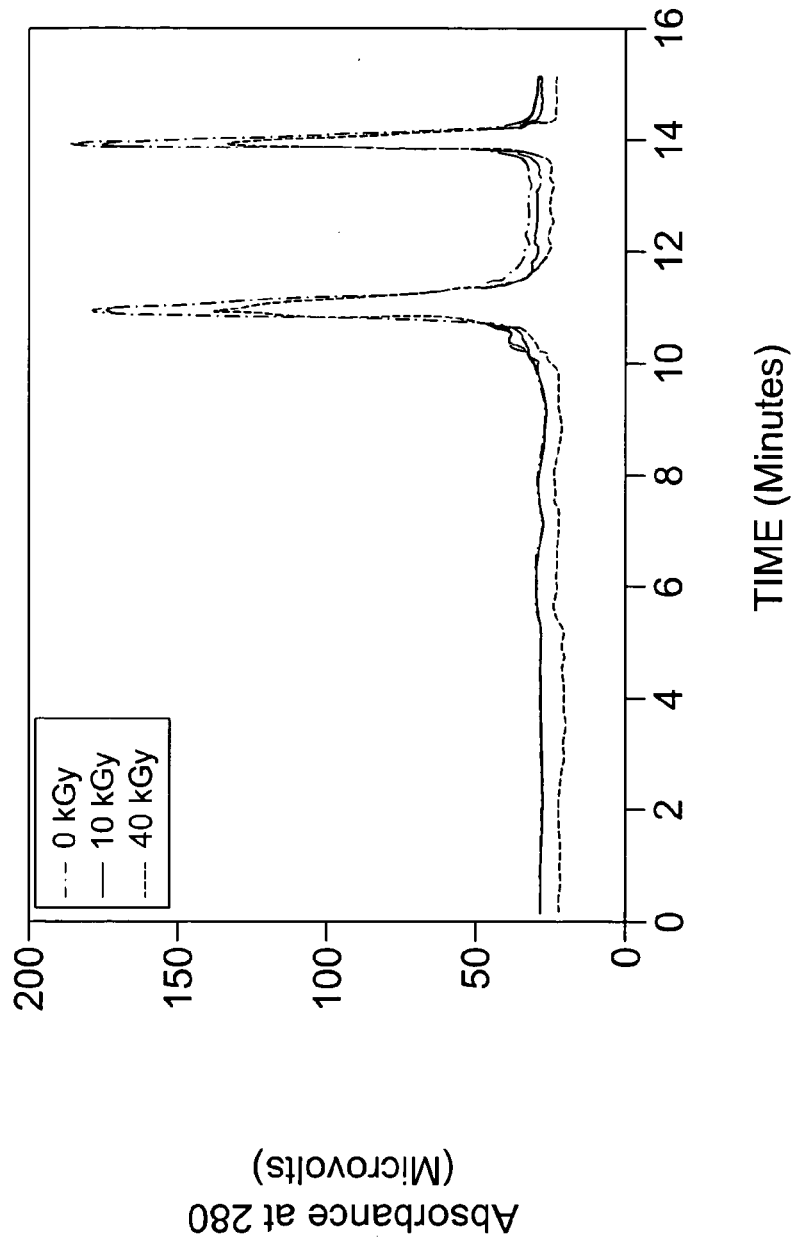
FIGS. 3A and 3B show lyophilized albumin (containing 5% urokinase) irradiated to a total dose of 10 or 40 kGy.
Figure 3B:
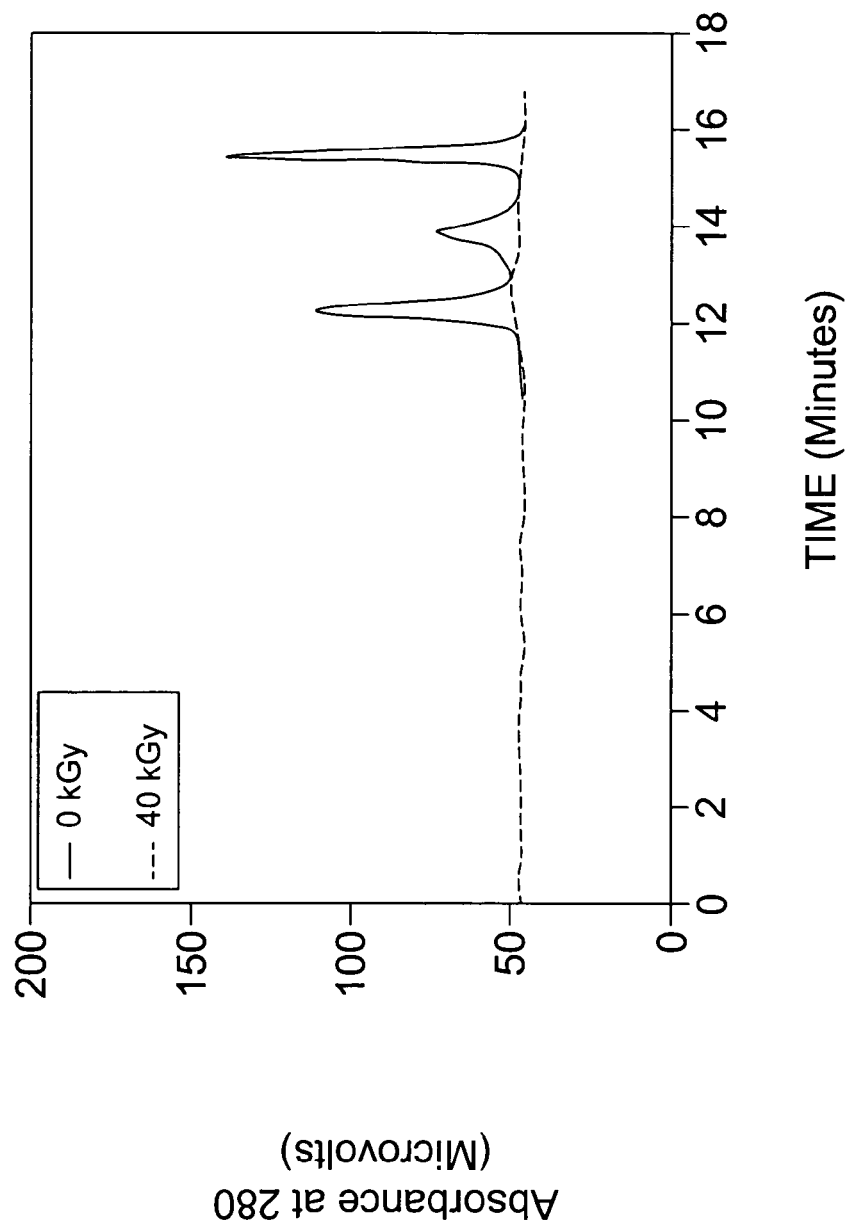

As shown in FIG. 3A, there was no change in the albumin when lyophilized and irradiated to either 10 kGy or 40 kGy total dose. In contrast, as shown in FIG. 3B, liquid albumin samples exhibited significant degradation when irradiated to 40 kGy total dose.

Example 4

In this experiment, samples of albumin solution (25%) were prepared and half of the samples sparged with Argon.

Samples were irradiated at a rate of 0.91, 0.92 or 1.01 kGy/hr to a total dose of 18.1, 23 and 30.4 kGy, respectively. Irradiated samples were assayed by SDS-PAGE for aggregation and fragmentation and by HPLSEC for dimerization and polymerization.

Figure 4A:
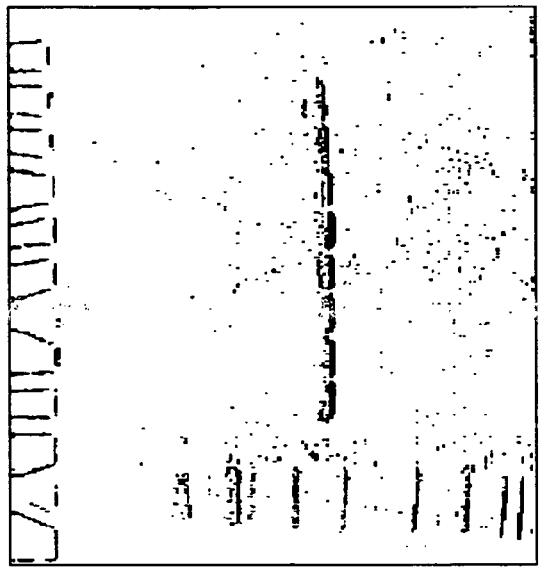
FIGS. 4A–4B show samples of albumin irradiated with or without prior sparging with argon.
Figure 4B:
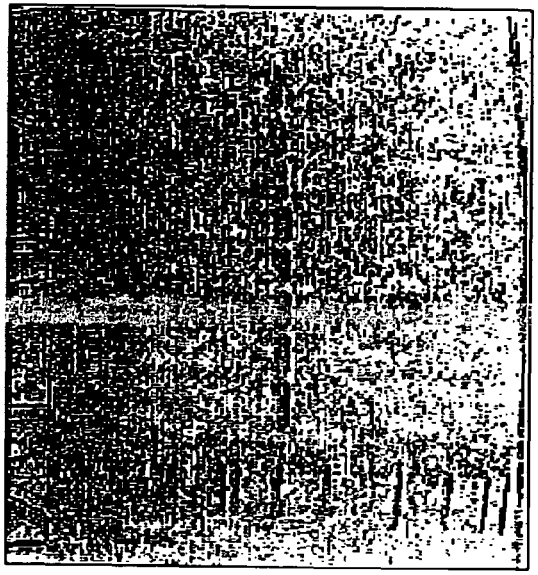

As shown in FIGS. 4A–4B, SDS-PAGE showed only small amount of fragmentation (doublet below 66 kDa band on reduced gel) and aggregation (116 kDa band on nonreduced gel), even for samples irradiated to a total dose of 30.4 kGy.

HPLSEC showed the following peaks:

| Total dose (kGy) | polymer (w/ Ar) | dimer (w/ Ar) | polymer (no Ar) | dimer (no Ar) |
|---|---|---|---|---|
| 0 (control) | 4.0% | 1.8% | 4.4% | 2.7% |
| 18.1 | 5.1% | 5.6% | 5.1% | 6.6% |
| 23 | 6.2% | 7.0% | 6.0% | 8.7% |
| 30.4 | 7.2% | 8.3% | 7.3% | 9.8% |

As Shown by HPLSEC, Less Dimerization Was Seen in Samples That Had Been Sparged With Argon Prior to Irradiation Example 5

In this experiment, plasma protein fractions were irradiated at −20° C. to varying total doses of radiation (10, 30 or 50 kGy).

Method

In glass vials, samples of a commercially available plasma protein fraction were prepared at a reduced solvent level of 9% water containing small amounts of ethanol and acetone. Samples were irradiated with gamma radiation at −20° C. at 1.608 kGy/hr. to a total dose of 10, 30 or 50 kGy and then assayed for structural integrity. Structural integrity was determined by SDS-PAGE and HPLSEC.

For SDS-PAGE, four 12.5% gels were prepared according to the following recipe: 4.2 ml acrylamide; 2.5 ml 4X-Tris (pH 8.8); 3.3 ml water; 100 µl 10% APS solution; and 10 µl TEMED, and placed in an electrophoresis unit with 1× Running Buffer (15.1 g Tris base; 72.0 g glycine; 5.0 g SDS in 1 l water, diluted 5-fold). Irradiated and control samples (1 mg/ml) were diluted with Sample Buffer (+/−beta-ME) in Eppindorf tubes and then centrifuged for several minutes. 20 µl of each diluted sample (~10 µg) were assayed.

For HPLSEC, 31 µg of each sample was loaded onto a Biosep SEC S3000 7.7×300 mm column in an Applied Biosystems 130A Separation System, flow rate 1 ml/min in 50 mM $Na_2HPO_4$ (pH 6.7), 100 mM NaCl.

Results

Figure 5A:
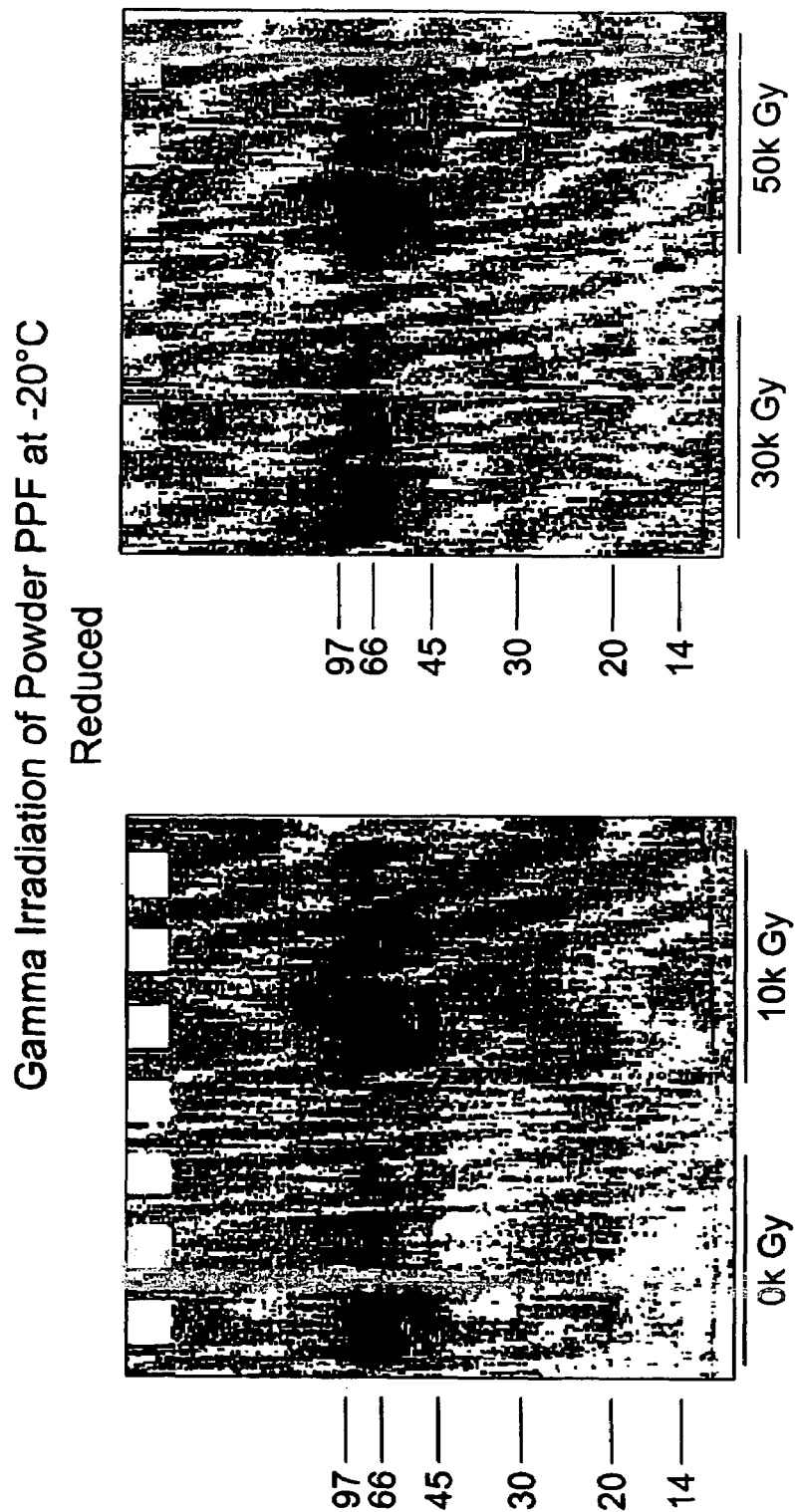
FIGS. 5A–5F show samples of albumin solution (25%) irradiated to a total dose of 18.1, 23 and 30.4 kGy and assayed by SDS-PAGE for aggregation and fragmentation and by HPLSEC for dimerization and polymerization
Figure 5B:
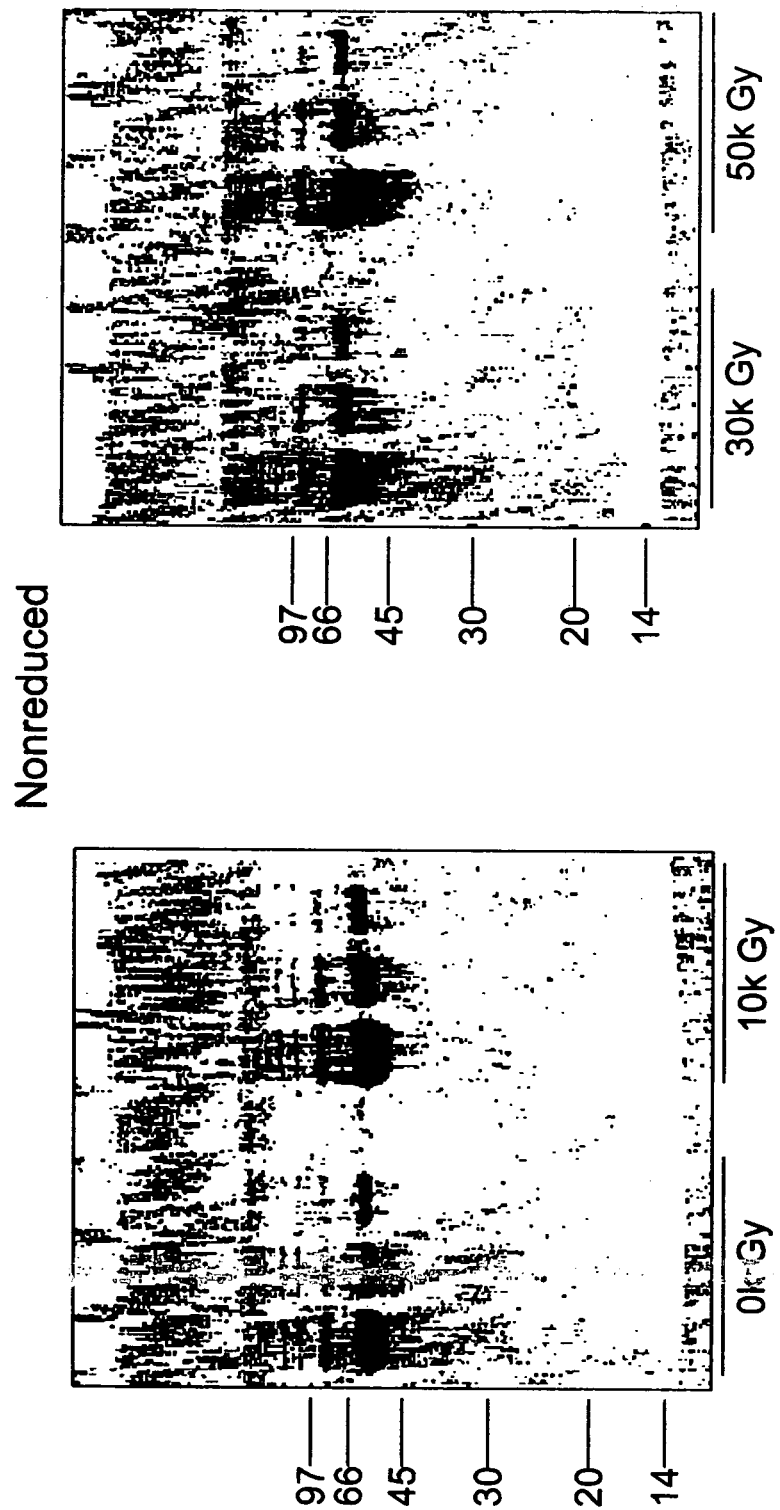
Figure 5C:
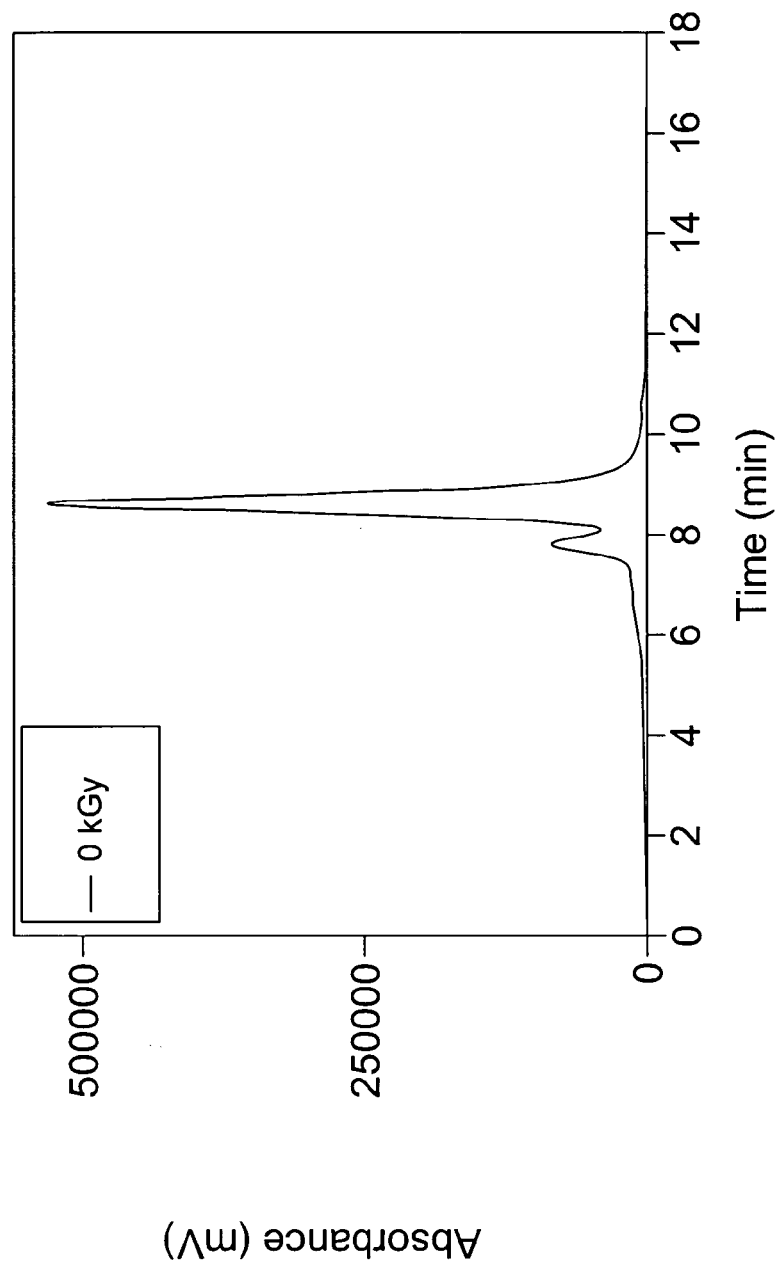
Figure 5D:
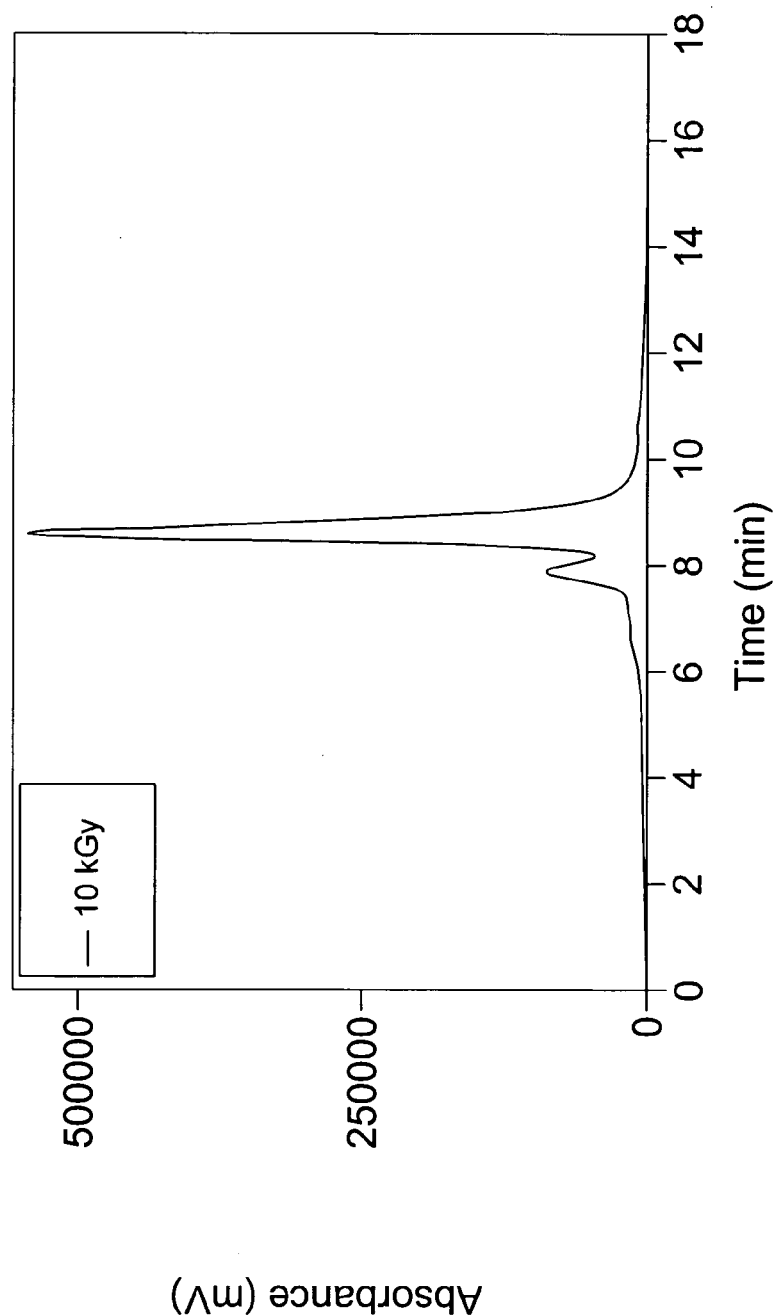
Figure 5E:
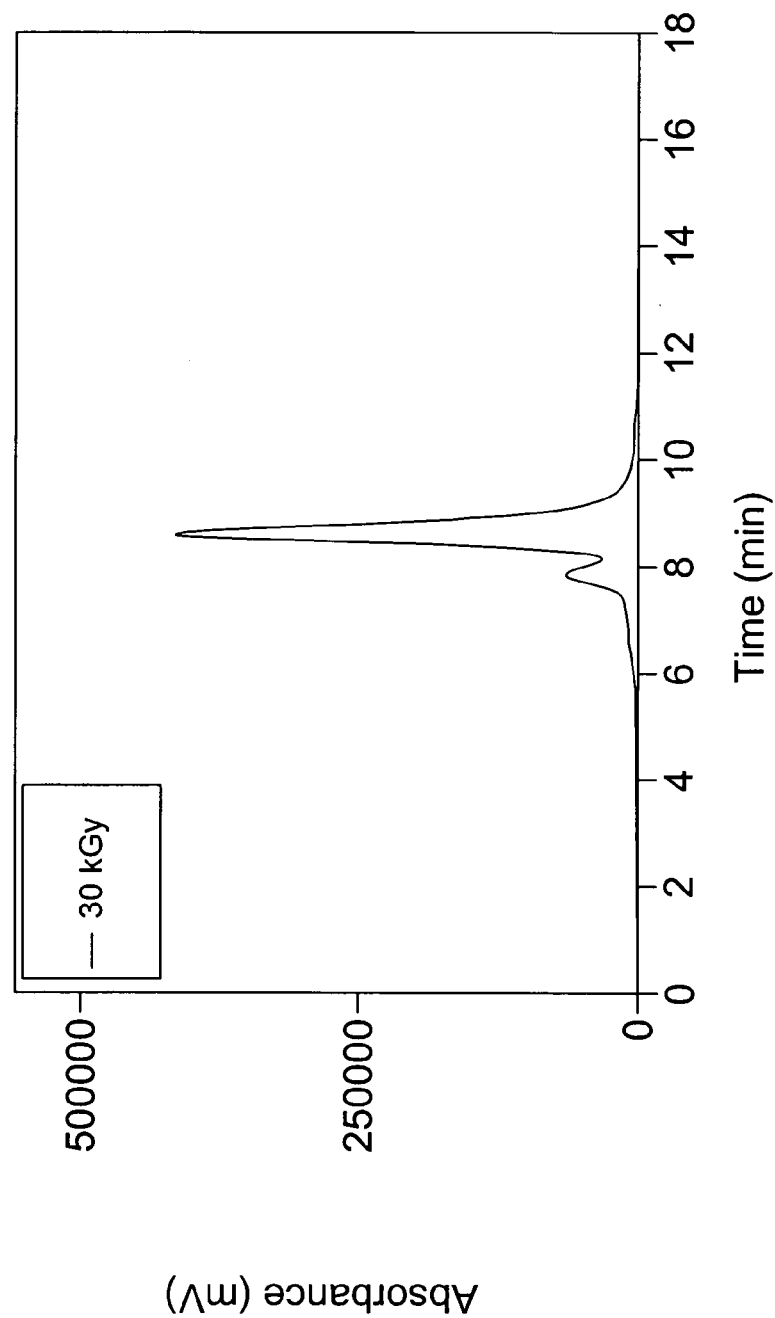
Figure 5F:
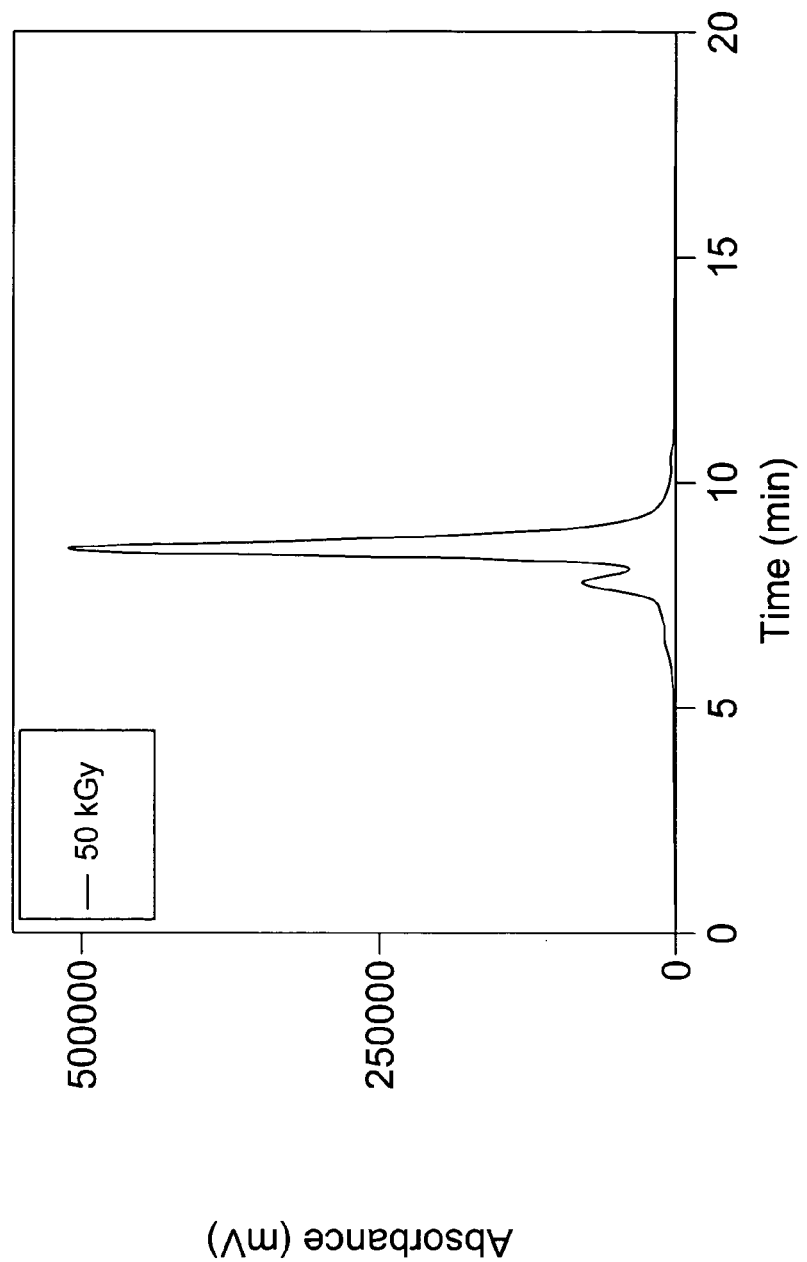

As shown in FIGS. 5A–5B, SDS-PAGE analysis demonstrates quantitative recovery of albumin monomer from the irradiated samples, even up to a total dose of 50 kGy of radiation. Similarly, as shown in FIGS. 5C–5F, HPLSEC indicates no increase in aggregation in any of the irradiated samples, even up to a total dose of 50 kGy of radiation.

Example 6

In this experiment, baby hamster kidney (BHK) cells obtained from the American Type Culture Collection were grown on media containing 20% (volume/volume) fetal bovine serum (FBS) and were slowly acclimated so that they were eventually able to grow with only 0.25% FBS (which is 5% of their normal FBS requirement). As then FBS was reduced, the media was supplemented with a commercial plasma protein fraction, either unirradiated or irradiated at a temperature of −20° C. at 1.608 kGy/hr. to a total dose of 50 kGy radiation, so that the plasma protein fraction was 0.3% weight/volume of the media (600 mg).

Results

There was no observable difference between BHK cells grown on media containing unirradiated plasma protein fraction and BHK cells grown on media containing plasma protein fraction that had been irradiated to a total dose of 50 kGy.

Example 7

In this experiment, plasma protein fractions containing porcine parvovirus (PPV) were irradiated at −80° C. to varying total doses of radiation.

Method

PPV stock #7 was prepared using 20%PEG8000 in 2.5M NaCl. The PEG-precipitated virus pellet was resuspended in PEG buffer (0.1M NaCl, 0.01 M Tris (pH 7.4), 1 mM EDTA).

Method 1

50 µl of PK-13 media or PPV stock #7 was added to 2 ml Wheaton vials and allowed to dry overnight at 40° C. 50 mg of a commercial plasma protein fraction was added once the liquid was dry and the vials were stoppered and then irradiated at −80° C. at a rate of 5.202 kGy/hr. to a total dose of 10, 30 or 45 kGy.

Method 2

50 mg of a commercial plasma protein fraction was placed in a 2 ml Wheaton vial and then mixed with either 150 µl of PK-13 media or 150 µl of diluted PPV stock #7 (100 µl PK-13 media +50 µl PPV) until dissolved. The vials were stoppered and then irradiated at −80° C. at a rate of 5.202 kGy/hr to a total dose of 10, 30 or 45 kGy.

TCID$_{50}$ Assay

850 μl of PK-13 media (DMEM ATCC#3020002, 10% FBS Gibco#26140079, 1% Pen/Step/L-Glutamine Gibco#10378016) was added to each vial to bring the volume to 1 ml. Samples were then filter sterilized using 13 mm filters (Becton Dickenson #4454) and 3 ml syringes.

PK-13 cells (ATCC#CRL-6489) were maintained in PK-13 growth media and seeded at 40% confluency the day prior to infection in 96-well plates. When cells were 70–80% confluent, 50 μl of the desired irradiated sample (containing either PK-13 media or diluted PPV stock #7) was added to 4 wells.

SDS-PAGE

Following irradiation, stock solutions of samples were prepared in HPLC water (10 mg/ml) and then diluted (2 mg/ml). Samples were then diluted 1:1 with 2× sample buffer (with or without DTT) and then loaded onto gels: 5 μg (10 μl) for samples from Method 1 and 10 μg (10 μl) for samples from Method 2.

Results

PPV treated plasma protein fractions irradiated at −80° C. according to Method 1 exhibited a viral kill of 3.9 logs using a total dose of 45 kGy (0.084 log/kGy). PPV treated plasma protein fractions irradiated at −80° C. according to Method 2 exhibited a viral kill of 5.54 logs (0.123 log/kGy). These results are shown graphically in FIG. 6. The irradiated plasma protein fractions did not cause any cytopathic effects in PK-13 cells.

Figure 6A:
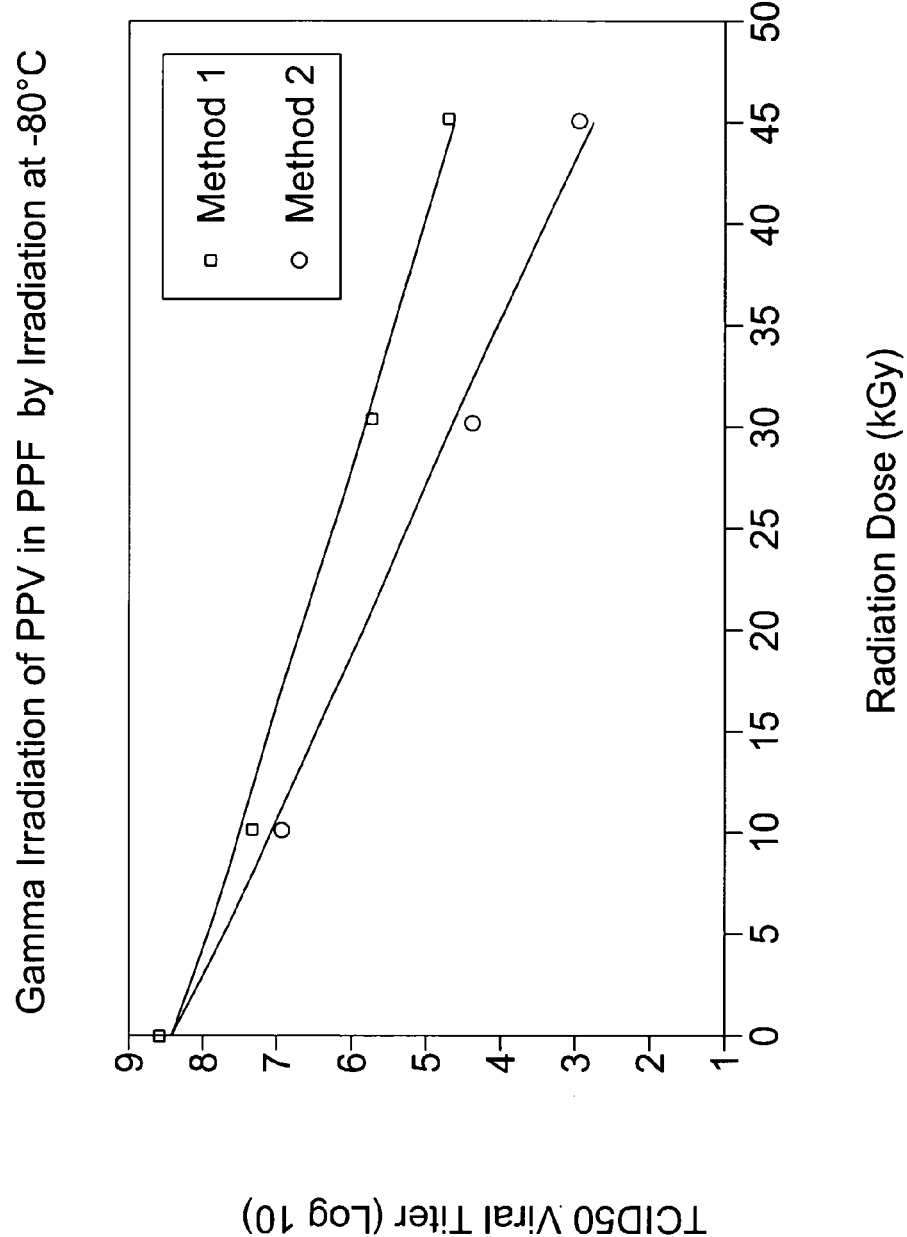
FIG. 6A is a graph showing the reduction in viral load in PPV-spiked plasma protein fractions following gamma irradiation.
Figure 6B:
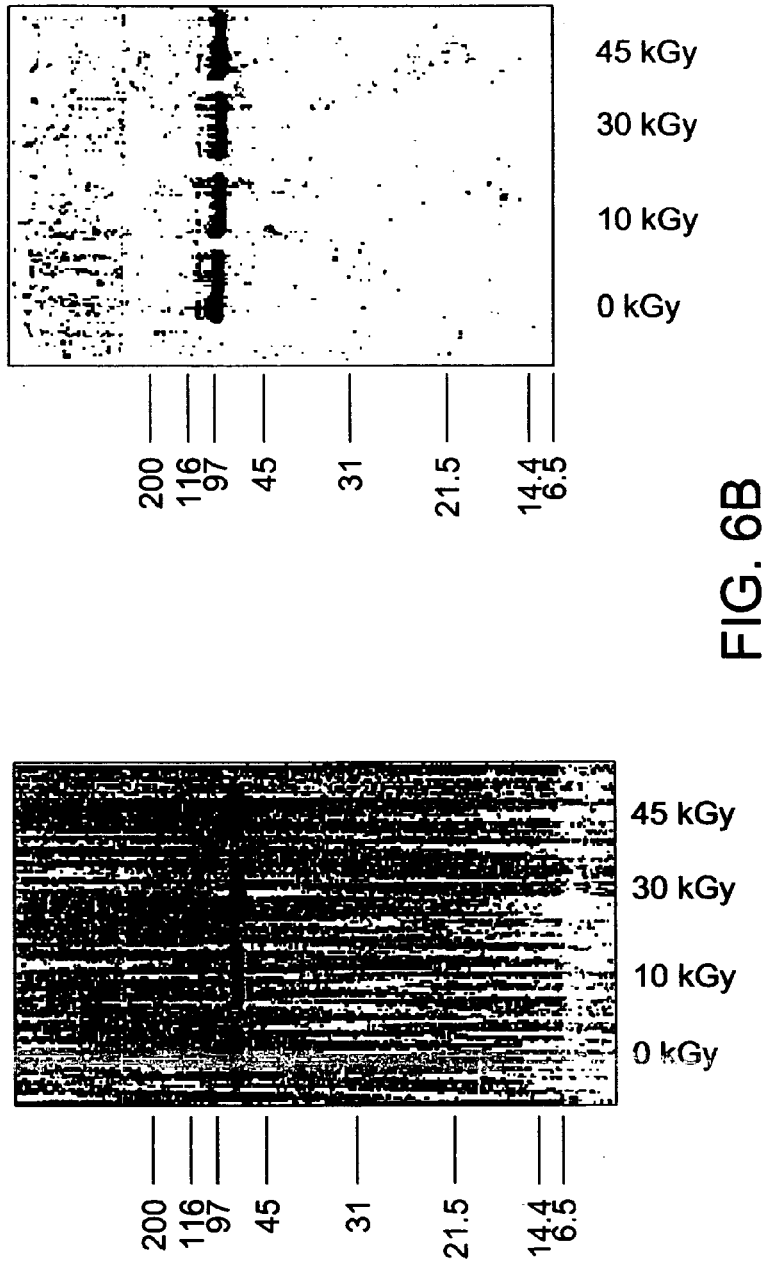

PPV treated plasma protein fractions irradiated at −80° C. were also assayed using SDS-PAGE. These results are shown in FIGS. 6B-6C.

Example 8

In this experiment, frozen preparations containing albumin and Factor VIII were irradiated.

Method

Samples containing albumin and Factor VIII were frozen and gamma irradiated to a total dose of 45 kGy.

Results

Figure 7:
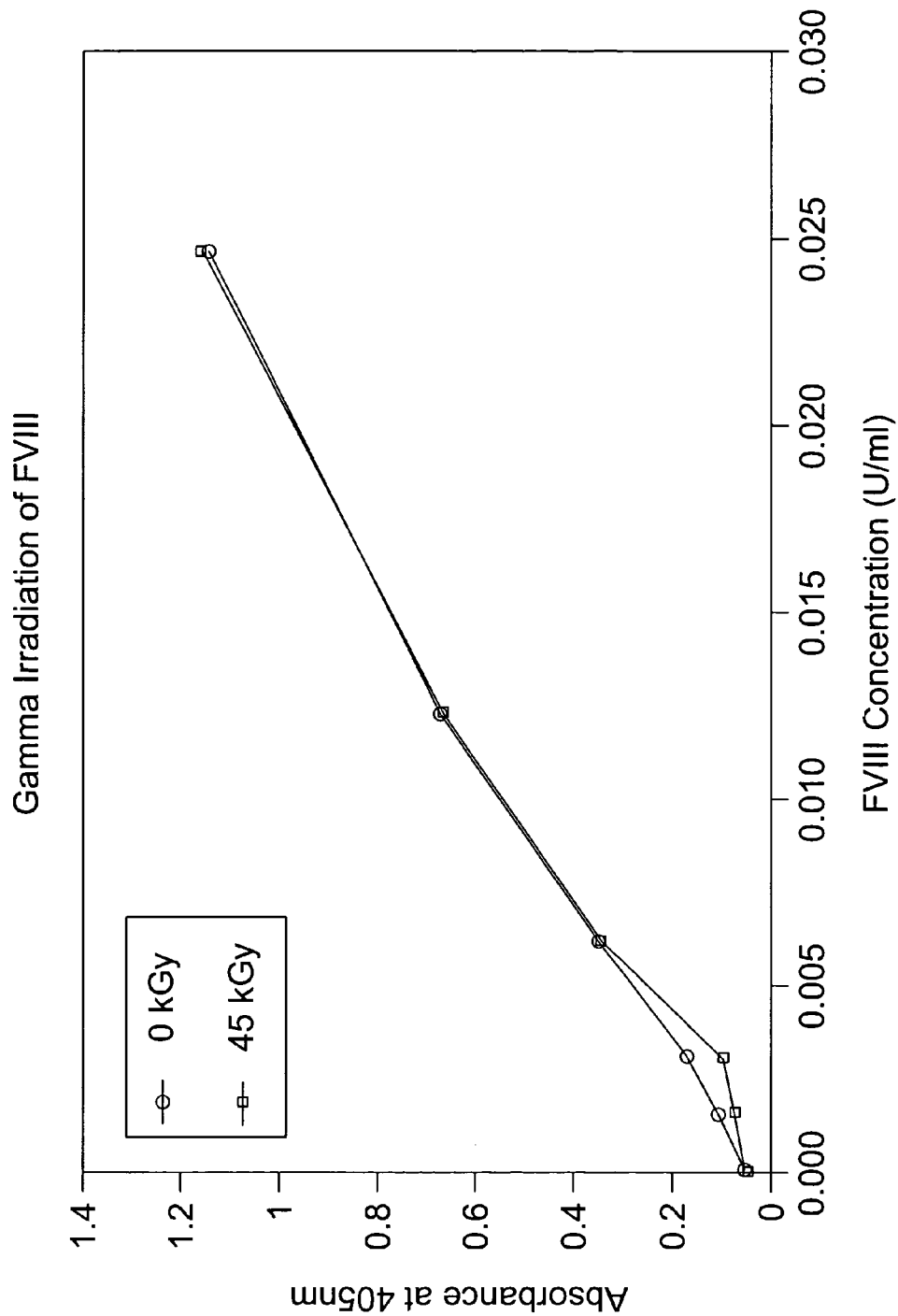
FIG. 7 is a graph showing the activity of Factor VIII in a preparation containing albumin and Factor VIII following gamma irradiation.

As shown in FIG. 7, there was no difference between the FVIII activity of the control (unirradiated) sample and the FVIII activity of the sample frozen and gamma irradiated to 45 kGy.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method for inactivating at least one biological contaminant or pathogen in a preparation containing albumin comprising irradiating said preparation with gamma radiation at a rate of greater than 3.0 kGy/hr for a time effective to inactivate at least one biological contaminant or pathogen in said preparation.

2. A method for inactivating at least one biological contaminant or pathogen in a plasma protein fraction preparation comprising irradiating said preparation with gamma radiation at a rate greater than 3.0 kGy/hr for a time effective to inactivate at least one biological contaminant or pathogen in said preparation.

3. A method for inactivating at least one biological contaminant or pathogen in a plasma protein fraction preparation comprising reducing the temperature of said preparation to a level effective to protect said preparation from gamma irradiation; and irradiating said preparation with gamma radiation at a rate of greater than 3.0 kGy/hr for a time effective to inactivate at least one biological contaminant or pathogen in said preparation.

4. The method according to claim 1, 2 or 3 further comprising reducing residual solvent present in said preparation to a level effective to protect said preparation from said gamma radiation.

5. The method according to claim 1, 2 or 3 further comprising adding to said preparation at least one stabilizer in an amount effective to protect said preparation from said gamma radiation.

6. The method according to claim 1 or 2, further comprising reducing the temperature of said preparation to a level effective to protect said preparation from said gamma radiation.

7. The method according to claim 1 or 2, further comprising at least two of
(i) reducing residual solvent present in said preparation to a level effective to protect said preparation from said gamma radiation;
(ii) adding to said preparation at least one stabilizer in an amount effective to protect said preparation from said gamma radiation; and
(iii) reducing the temperature of said preparation to a level effective to protect said preparation from said gamma radiation.

8. The method according to claim 2 or 3 wherein said plasma protein fraction comprises albumin.

9. The method according to claim 2 or 3 wherein said plasma protein fraction further comprises at least one protein selected from the group consisting of a coagulation protein, a lipoprotein and a complement protein.

10. The method according to claim 7, wherein said coagulation protein is at least one selected from the group consisting of Factor VII, Factor VIII Factor D( and von Willebrands factor.

11. The method according to claim 2 or 3 wherein said plasma protein fraction further comprises at least one biological material selected from the group consisting of hemoglobin, alpha-globulin, beta-globulin and gamma-globulin.

12. The method according to claim 1 or 2 wherein said rate is greater than about 6.0 kGy/hr.

13. The method according to claim 1 or 2 wherein said rate is greater than about 18 kGy/hr.

14. The method according to claim 1 or 2 wherein said rate is greater than about 30.0 kG/hr.

15. The method according to claim 4 wherein said residual solvent is water.

16. The method according to claim 4 wherein said residual solvent is an organic solvent.

17. The method according to claim 4 wherein said residual solvent is reduced by a method selected from the group consisting of lyophilization, concentration, addition of solute, chemical extraction, spray-drying and vitrification.

18. The method according to claim 4 wherein the content of said residual solvent present in said preparation after said reduction is less than about 10%.

19. The method according to claim 4 wherein the content of said residual solvent present in said preparation after said reduction is less than about 5%.

20. The method according to claim 5 wherein said at least one stabilizer is an antioxidant.

21. The method according to claim 5 wherein said at least one stabilizer is a free radical scavenger.

22. The method according to claim 5 wherein said at least one stabilizer is selected from the group consisting of ascorbic acid or a salt or an ester thereof; DMSO, mannitol, trehalose, glutathione; 6-hydroxy-2,5,7,8-tetramethyl-chrom-2-carboxylic acid; uric acid or a salt or ester thereof methionine; histidine; N-acetyl cysteine; lipoic acid; sodium formaldehyde sulfoxylate and gallic acid or a salt or an ester thereof.

23. The method according to claim 3 wherein said temperature is reduced below ambient temperature.

24. The method according to claim 3 wherein said temperature is reduced below the freezing point of said preparation.

25. The method according to claim 3 wherein said temperature is reduced below the eutectic point of said preparation.

26. The method according to claim 3 wherein said temperature is reduced below 0° C.

27. The method according to claim 3 wherein said temperature is reduced below minus 40° C.

28. The method according to claim 3 wherein said temperature is reduced below minus 60° C.

29. The method according to claim 1, 2 or 3 wherein said gamma irradiation is administered for a time effective to sterilize said preparation.

30. The method according to claim 1 wherein the preparation containing albumin is selected from the group consisting of Albuminar®, Buminate®, Albutein® and Albumarc®.

31. The method according to claim 2 or 3 wherein the plasma protein fraction preparation is selected from the group consisting of Plasma-Plex®, Protenate® and Plasmatein®.

32. The method according to claim 2 or 3 wherein the plasma protein fraction preparation is Plasmanate®.

33. A biological composition produced by any of the methods of claim 1, 2 or 3.

34. The composition of claim 33 wherein the composition is sterile albumin.

35. The composition of claim 33 wherein the composition is sterile plasma protein fraction.

36. The method of claim 5 wherein said at least one stabilizer is DMSO.

37. The method of claim 5 wherein said at least one stabilizer is mannitol.

38. The method of claim 5 wherein said at least one stabilizer is trehalose.

* * * * *